US007197884B2

(12) United States Patent
Jones et al.

(10) Patent No.: US 7,197,884 B2
(45) Date of Patent: Apr. 3, 2007

(54) ASSEMBLY AND METHOD FOR CRYO-PRESERVATION OF SPECIMENS IN A CRYOGEN-FREE ENVIRONMENT

(75) Inventors: Catherine Jones, Whitmore Lake, MI (US); Mohinder Kaur, Hampton (GB)

(73) Assignees: Christopher Jones, Baltimore, MD (US); Davinder Kaur, London (GB)

( * ) Notice: Subject to any disclaimer, the term of this patent is extended or adjusted under 35 U.S.C. 154(b) by 252 days.

(21) Appl. No.: 10/947,453

(22) Filed: Sep. 23, 2004

(65) Prior Publication Data

US 2005/0188705 A1 Sep. 1, 2005

Related U.S. Application Data

(60) Provisional application No. 60/548,611, filed on Mar. 1, 2004.

(51) Int. Cl.
*F25B 9/00* (2006.01)
(52) U.S. Cl. ........................................................ 62/86
(58) Field of Classification Search ............... 62/6, 62/51.1, 86, 434, 467
See application file for complete search history.

(56) References Cited

U.S. PATENT DOCUMENTS

| 4,292,062 | A | * | 9/1981 | Dinulescu et al. | ............... | 62/7 |
| 4,566,291 | A | * | 1/1986 | Halavais | ...................... | 62/402 |
| 4,575,386 | A | * | 3/1986 | Hamers | ........................ | 62/614 |
| 5,347,819 | A | * | 9/1994 | Saji et al. | ...................... | 62/610 |
| 5,447,033 | A | * | 9/1995 | Nagao et al. | ..................... | 62/6 |
| 5,709,203 | A | * | 1/1998 | Gier | ........................ | 128/201.21 |
| 5,816,052 | A | * | 10/1998 | Foote et al. | .................. | 62/51.1 |
| 6,122,920 | A | * | 9/2000 | Hill et al. | ..................... | 62/55.5 |
| 6,360,730 | B1 | * | 3/2002 | Koethe | ........................ | 123/541 |
| 6,380,544 | B1 | * | 4/2002 | Broerman | .............. | 250/370.15 |

FOREIGN PATENT DOCUMENTS

JP 63-315868 A * 12/1988

* cited by examiner

*Primary Examiner*—Mohammad M. Ali
(74) *Attorney, Agent, or Firm*—William W. Jones

(57) ABSTRACT

A cold cryostorage assembly includes a storage chamber in which specimens can be cryo-preserved. Specimen samples are stored in a vacuum so as to minimize the risk of sample contamination. The specimen samples can be cooled and warmed at adjustable controlled rates which best suit the specimen samples in question. The storage chamber can be cooled to temperatures as low as −269° C. without the use of a cryogen that contacts the specimen sample containers. The specimens can be inserted into and/or removed from the storage chamber at individually programmed variable rates by means of an automated specimen-handling component of the assembly. The specimen handling component of the assembly can be operated by remote control, or even over the internet. The storage chamber is evacuated, and in any case, it does not involve the use of a cryogen in direct contact with sample containers in the storage chamber. The cryogen is contained inside of closed heat exchangers that are disposed in the storage chamber.

16 Claims, 19 Drawing Sheets

ASSEMBLY AND METHOD FOR CRYO-PRESERVATION OF SPECIMENS IN A CRYOGEN-FREE ENVIRONMENT

This application claims the benefit of U.S. Ser. No. 60/548,611, filed Mar. 1, 2004.

TECHNICAL FIELD

This invention relates to an assembly and method for cryogenically preserving specimens at temperatures as low as 4K (−269° C.) without immersing the specimen samples directly in a liquid or a gaseous cryogen. The assembly includes a specimen insertion and retrieval system which can be operated by remote control.

BACKGROUND ART

Biological specimens such as blood, sperm, ova, embryos, nucleotide strands and enzymes, multi cellular specimens such as skin, and the like, are conventionally stored in racks or trays which are placed in a cryogenically cooled chamber either manually or robotically. The specimens or samples are themselves placed in ampules or vials which are then placed on the racks or trays that are immersed in the cryogenic liquid or vapor. The ampules and/or vials are typically provided with color coded dosures that can be manually coded by using an ink marker or bar coded so as to identify the contents of the ampules or vials.

U.S. Pat. No. 4,377,077 describes a cryo-unit which includes a refrigerant unit in which specimens or samples to be cryo-preserved are placed, which refrigerant unit is then stored in another refrigerator.

U.S. Pat. No. 5,233,844 describes an automated cryo-unit which has a large number of moving parts. The components of this cryo-unit are particularly prone to failure at cooling temperatures due to the generation of thermoelastic stresses which result from differential thermal contraction during cool down from ambient temperatures to operating temperatures. This unit also suffers from the formation of water ice due to the lack of a vacuum seal in the cryochamber. This unit utilizes liquid cryogens and thus its operating lifetime is limited by the supply of those cryogens. While it is understood that these cryogens are to be replenished, a catastrophic failure mechanism nonetheless exists whereby the samples would be inadvertently warmed up should the supply of these cryogens be interrupted. Since this unit uses liquid nitrogen as its cryogen, its base temperature is limited to −196° C.

U.S. Pat. No. 4,969,336 discloses a cryo-unit which also has a large number of moving parts and uses liquid cryogens to reach its operating temperatures. The operating temperatures and reliability of storage are thus limited by these liquid cryogens.

U.S. Pat. No. 5,921,102 discloses a cryo-unit which uses a liquid cryogen wherein the specimen samples are placed in the liquid cryogen or its vapors during storage. The cryogen used is typically nitrogen. This unit thus can result in undesirable cross contamination between the samples and the cryogen. The use of liquid cryogens also limits the storage temperatures and the storage reliability of the specimen samples.

U.S. Pat. No. 6,467,285 discloses an automated storage and retrieval apparatus for low temperature freezers that are used to preserve specimen samples. Liquid carbon dioxide or liquid nitrogen is used as a cryogen to obtain these temperatures. Specimens to be stored are robotically inserted into a chamber in the freezer where the humidity is reduced to guard against the occurrence of frost, and then the specimens are moved into a storage chamber in the freezer. The specimens are robotically placed on a carousel in the storage chamber. The specimen holders are bar coded so that they can be retrieved and properly identified. The storage temperatures of the freezer are limited by the use of a liquid cryogen to obtain operating temperatures. This patent does not suggest any way to achieve freezer operating temperatures in the range of −140° C. to −196° C. which it states are desirable. In fact its operating temperatures are between −50° C. and −90° C. Also, the immersion of the specimen samples in liquid cryogens raises the possibility that the specimen samples will become cross contaminated by the cryogen.

It is noted that all of the above-noted cryogenic freezers have operating temperatures that are limited by the immersion of the samples in liquid nitrogen.

Because molecular processes slow down at lower temperatures, it would be desirable to provide a cryogenic storage assembly which can achieve operating temperatures that are colder than those that can be achieved with the immersion of the samples in liquid nitrogen. It would also be desirable to preserve the specimen samples in a vacuum so as to reduce sample crystallization and contamination.

DISCLOSURE OF THE INVENTION

This invention relates to an automated cryogenic freezer assembly; can operate at evenly distributed storage temperatures as low as 4K (−269° C.); is dependable at such low operating temperatures; can provide rapid and accurate cooling and heating between operating and ambient temperatures at controlled rates; includes a vacuum-sealed cryo-chamber to ensure a zero humidity storage environment; minimizes storage temperature fluctuations during specimen sample retrieval; and provides rapid access to all of the specimens in the cryochamber. The assembly also preferably includes redundant cryogen compressors for increased reliability.

The extremely low cryogenic temperatures that can be achieved in connection with this invention are accomplished by using a closed cycle thermomechanical refrigeration system that performs work on a cryogenic fluid. The system includes redundant external compressors which can compress a cryogenic fluid, and internal heat exchangers through which the cryogenic fluid is circulated. In a system that achieves the 4K operating temperature, the operative cryogenic fluid is helium. The assembly of this invention can utilize one or more cryogenic stages. By "cryogenic stages" we mean a set of cryogenic components which are at a common cryogenic temperature. A specific example of a cryogenic stage would include a cryogen expansion space that is connected to a cryo-cooler tip, which is the coldest part of the heat exchanger, and wherein the cryogen will ultimately liquefy, and a specimen sample support, which are maintained at a common cryo-temperature. In an assembly having a plurality of cryogenic stages, there could be a single primary cryogen compressor and a plurality of heat exchangers associated with that compressor. This arrangement would be useful for a single primary cryo-cooler assembly. The assembly could also be formed with redundant cryogenic stages for purposes of enhancing system reliability. The redundant stages could have their own compressors.

The cryogenic fluid undergoes a thermodynamic cycle wherein it is ultimately compressed and cooled to its liquid state, expanded back to its gaseous state, recompressed and cooled to its liquid state, so that the cycle includes alternating compression/cooling and expansion/warming of the cryogen, which in the typical system, would be the Gifford-MacMahon cycle, which is a closed loop thermodynamic cycle which makes use of valves. Coolers employing this cycle are available, inexpensive, and quite reliable. Multi staging of at least two heat exchangers would be preferred, however, the two stages can be integrated within a single cooler so that there would be negligible complexity in including the two cryogenic stages in a single cooler. By using a multistage system, the temperature of the cryogen can be lower than with a single stage cooler for the same compressor power. In order to obtain additional cooling at the 4K temperature, a Joule-Thomson expansion final stage can be added wherein the cryo fluid, helium, is pre cooled to below its inversion temperature so that expansion of the cryo fluid results in further cooling. The Gifford-MacMahon coolers would serve as precoolers in order to cool the working fluid to temperatures which are significantly below its thermodynamic inversion temperature. It may be expeditious to utilize a pulse-tube cooler with fewer moving parts instead of the Gifford-MacMahon coolers, however, for some purposes, the Gifford-MacMahon coolers are preferred for reasons of reliability and greater refrigeration capability.

The cryogen which can be helium, nitrogen, neon, or the like, is constantly recirculated between a compressor, and one or more heat exchangers, the latter of which are disposed in a first chamber of the assembly, in which first chamber the specimens to be cooled are placed. The aforesaid first chamber is evacuated so as to reduce thermal conductance inside of the chamber to walls thereof and to minimize contaminants therein. The walls of the first chamber are insulated with several layers of low heat conductance materials such as aluminized MYLAR(™). Thus, in the coldest embodiment of the system, a cryogen such as helium is compressed and is circulated through a heat exchanger that ultimately cools the cryogen to a liquid state, and therefore also cools anything that is thermally attached to this final stage of the cooler, i.e., the containers in which the samples to be cryogenically preserved are placed. The compressed cryogen is continuously expanded in the expansion space in the heat exchanger and then returned to the compressor to be recompressed.

In one embodiment, the cryogenic cooler structure includes two chambers. A lower chamber in the cooler structure contains the heat exchangers and also a movable platform that supports the specimen sample containers. An automated cooling version of the cooler structure may also include an upper chamber that contains a specimen sample tube transfer device. The lower chamber is insulated so as to minimize heat loss therefrom. The upper and lower chambers are separated by a wall that includes a central window that can be selectively opened and closed so as to allow the sample tube transfer device access to the lower chamber to load or remove sample containers from the sample tube support platform. By employing a self contained supply of the cryogen which never comes into direct contact with the sample tubes, the assembly of this invention does not require periodic replenishment of the cryogen used, and does not present any risk of contamination of the specimen samples by the cryogen. By evacuating the specimen sample chamber, heat input into the sample is minimized. The evacuation of the chamber also means that there is no gaseous medium at all which might cause cross contamination of the sample (s). The reduction of heat input into the specimen sample-containing chamber is further enhanced by the insulating materials described herein.

In a somewhat simplified embodiment of the cooler assembly of this invention suitable for home use, the airlock system and the two separate chambers can be eliminated in order to reduce cost and complexity. In consequence, the automated sample extractor component can also be eliminated solely to reduce cost and complexity. If cost allows, however, it is preferable to include the airlock system in order to prevent the other samples from warming during sample extraction or retrieval. In any case, key advantages of this invention over the prior art are the ability to achieve extremely low specimen sample preservation temperatures; the elimination of direct contact between liquid cryogens and the sample containers; and the resultant elimination of the need to ensure a constant supply of the cryogens.

It is therefore an object of this invention to provide an assembly of the character described wherein extremely low sample preservation temperatures can be achieved and maintained.

It is a further object of this invention to provide an assembly of the character described which prevents contamination of the specimens being cooled by the cryogen being employed by the assembly.

It is another object of this invention to provide an assembly of the character described which does not require periodic replenishment of the cryogen in question.

It is an additional object of this invention to provide an assembly of the character described which is evacuated so as to minimize heat transfer into the specimen sample containers and into the heat exchangers.

It is still another object of this invention to provide an assembly of the character described which can cool and warm specimen samples at controlled rates prior to and subsequent to the cryo-preservation of the samples.

It is yet another object of this invention to provide an assembly of the character described which improves the temperature stability of the samples at the cryogenic temperature through use of materials which have high thermal capacity and which are thermally connected to the samples.

Another object of this invention is to provide an assembly of the character described wherein samples are pre-cooled through the use of pre-cooling upper chamber in the assembly.

BRIEF DESCRIPTION OF THE DRAWINGS

These and other objects and advantages of the invention will become more readily apparent from the following detailed description of an embodiment of the invention, when taken in conjunction with the accompanying drawing in which.

DETAILED DESCRIPTION OF SPECIFIC EMBODIMENTS OF THE INVENTION

Figure 1:
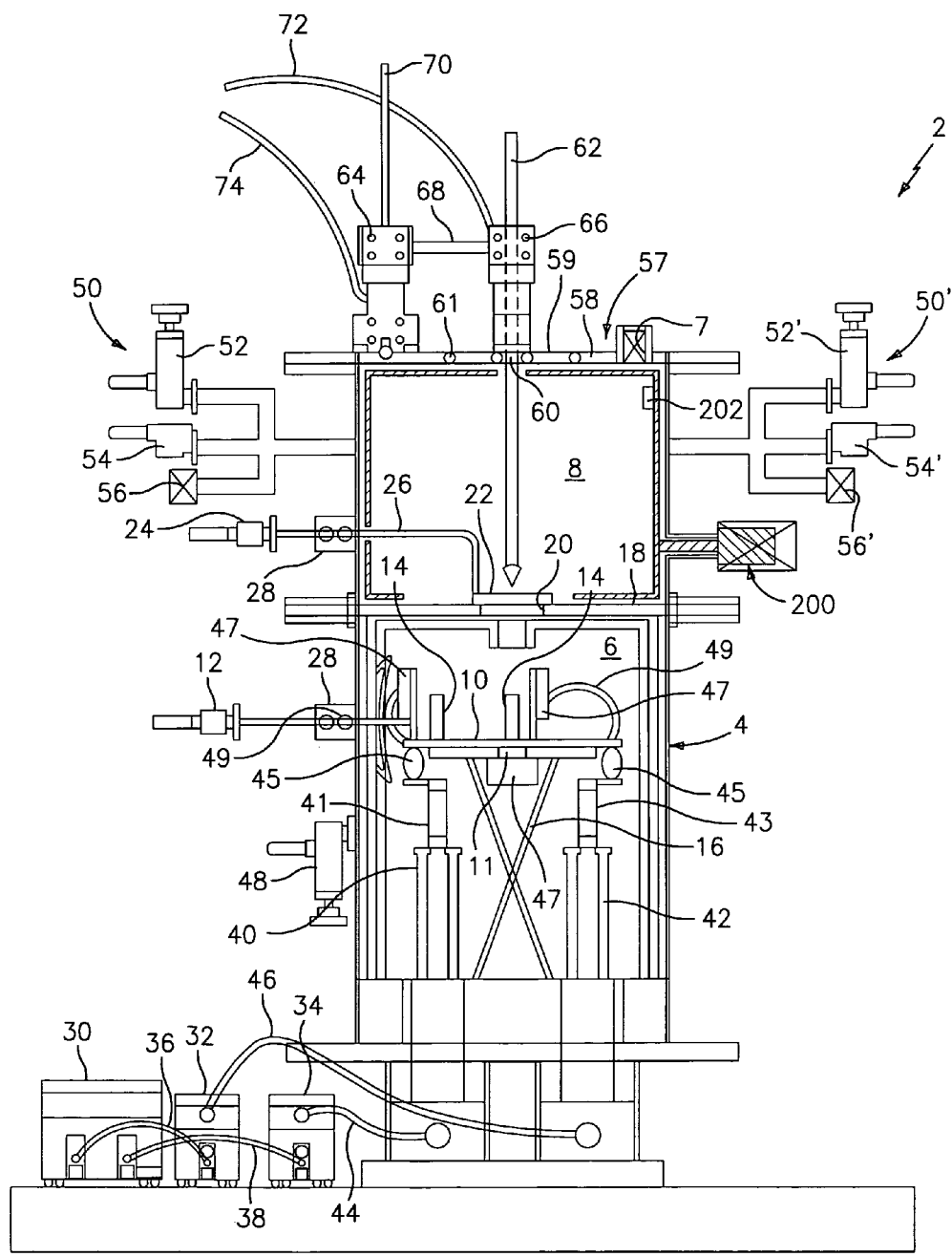
FIG. 1 is a somewhat schematic side sectional and elevational view of a first embodiment of a cryogenic preservation assembly formed in accordance with this invention.

Referring now to the drawings, FIG. 1 shows a first embodiment of a cryo-preservation assembly, which is denoted generally by the numeral 2, and which is formed in accordance with this invention. The assembly 2 includes a housing 4 that has two chambers 6 and 8. The chamber 6 is a cooling chamber in which the specimen samples to be preserved are stored; and the chamber 8 is a specimen sample container retrieval chamber into which frozen samples are retrieved from the chamber 6. A pre-cooler 200 is used to pre-cool the upper chamber 8 after placing specimen samples in the upper chamber of the assembly 2; and a heater 202 is used to warm the upper chamber 8 prior to removing specimen samples from the upper chamber of the assembly 2. The cooling chamber 6 contains a movable specimen sample container stage 10 which is formed from a high thermally conductive material, such as copper, or the like. The stage 10 can be selectively moved by means of a stage actuator 12 which can translate the stage 10 to selected positions. Specimen sample containers 14 are positioned on the stage 10 during the cryo-preservation procedure. The stage 10 is disposed on a support structure 16. The chambers 6 and 8 are separated by a plate 18 that includes an access window 20. The access window 20 is selectively sealed by a plate 22 which can be moved between a window-closed position shown in FIG. 1 and an open position shown in FIG. 2 by a movable actuator 24 which is connected to the plate 22 by a rod 26. The rod 26 moves back and forth through a sealed fitting 28 mounted on the housing 4.

The assembly 2 also includes a water cooler 30 that is operatively connected to coolant compressors 32 and 34 via lines 36 and 38. The coolant compressors 34 and 32 are connected to heat exchangers 40 and 42 via lines 44 and 46 respectively. An initial portion of the heat exchangers forms a cryogen expansion section thereof wherein the compressed cryogen stream will expand during the cool down cycle of the heat exchangers. The heat exchangers 40 and 42 can be formed from copper and are disposed in the cooling chamber 6. The heat exchangers 40 and 42 are in heat exchange relationship with the stage 10 so as to cool the stage 10 directly via heat switches 41 and 43 respectively, which heat switches 41 and 43 thermally connect or isolate the cold side of the respective heat exchangers 40 and 42, respectively, from the specimen sample container stage 10. The heat switches 41 and 43 are switches that switch on and off, as commanded by the system controller. In the "on" state, the heat switch creates a high thermally conductive path from the cooler tip to the sample container support 10, and thus to the sample containers 14. When in the "on" state the switches 41 and 43 connect the cooler tips so as to interconnect the cryogen expansion spaces in the heat exchangers with the coldest side (the "cold side") of the of the heat exchangers 40 and 42 to the sample container support 10. In the "off" state, the heat switches create a poor thermally conductive path from the cooler tips to the sample container support 10. If the primary cooler 40 fails, then the heat switch 41 will be turned "off", and the secondary cooler 42 will be activated and the heat switch 43 will be turned "on". Turning the heat switch 41 off lessens the heat onto, and therefore the rate of warming, of the support 10 and specimen samples 14 from the failed cooler 40. The aforesaid procedure ensures that cooling of the samples 14 continues without interruption. The heat switches 41 and 43 are thermally connected to the support 10 via thermally conductive braided links 45 which may be formed from copper, or some other thermally conductive material. The support 10 is thermally connected to thermal storage units 47 via respective flexible braided links 49 which are connected to the support 10. The thermal storage units 47 can be formed from rare earth metals. A thermal storage unit 47 also contacts the underside of the support 10. A contaminant absorbent material 11 may be disposed on the underneath surface of the support 10, and is operative to absorb any contaminants that may enter the chamber 6. The contaminant absorbent material 11 can be charcoal, and will absorb contaminants such as water and/or residual air. The chamber 8 is also provided with a safety valve 7 which guards against over pressurization of the chamber 8 during operation of the assembly 2.

The compressors 32 and 34 are operative to compress a gaseous cryogen coolant such as nitrogen, helium. The compressed cryogen is then pumped into the heat exchangers 40 or 42, in the coldest parts of which it is expanded to lower the temperature of the stage 10. The compressed cryogen will expand in the heat exchangers 40 or 42 as it warms up, and the expanded cryogen will be pumped back into the compressors 32 or 34 so as to be re-pressurized and then will be pumped back into the heat exchangers 40 or 42 where it continues with the cooling process. Thus the compressed cryogen flows into the heat exchangers, is expanded in the heat exchangers to lower the temperature of the heat exchangers and the interior of the container 2, and flows back through the heat exchangers to the compressor where it is recompressed. The aforesaid cycles are continuously repeated to achieve the desired cryogenic cooling temperatures of the specimen samples. In certain cases, the temperature in the heat exchanger will reach a cryogen liquefaction temperature prior to reaching the target temperature, wherein the compressed cryogen will be liquefied in the heat exchangers 40 or 42. This liquefaction temperature for helium is −268° C., for neon is −246° C., and for nitrogen is −153° C. all at atmospheric pressure. The compressors 32, 34 and their associated heat exchangers 40, 42 are used in alternating fashion so that each one serves as a backup for the other. During operation of the assembly 2, the water cooler 30 pumps cold water into the compressors 32, 34 so as to pre cool the cryogen exiting the compressors and to prevent overheating of the pumps of the compressors 32, 34.

During operation of the assembly 2, the coolant chamber 6 is evacuated so as to minimize air conducted thermal heating into the chamber 6. The chambers 6 and 8 are also thermally insulated by a plurality of aluminized poly amide sheets 3, which are sold by DuPont under the trademark MYLAR, so that thermal losses between an inner radiation shield 5 and the outer chamber wall 4 are reduced to a minimum, thereby further reducing thermal transfer between the chamber 6 and ambient surroundings (see FIG. 2). There is also an intermediate thermal shield connected to the intermediate cooling stage of each cooler.

To evacuate the chamber 6, it is accessed by a solenoid valve-controlled passage 48 which can be selectively opened and closed to evacuate the chamber 6 (open) and to isolate the chamber 6 (closed). A vacuum pump (not shown) is operatively connected to the passage 48. During operation of the assembly 2, the retrieval chamber 8 is periodically evacuated, and re-pressurized. In order to accomplish the aforesaid, the chamber 8 is provided with a first evacuation and pressurization port assembly denoted generally by the numeral 50, and a second redundant such assembly denoted generally by the numeral 50'. Each of the assemblies 50 and 50' includes respective solenoid operated evacuating valves 52 and 52' for selectively evacuating the chamber 8 to the same pressure that exists in the chamber 6; solenoid operated pressure valves 54 and 54' for selectively pressurizing the chamber 8 up to slightly above ambient temperature using a filtered dried pressurization gas such as nitrogen; and pressure gauges 56 and 56' for monitoring the pressure in the chamber 8.

The chamber 8 has a top cover plate assembly 57 which includes an annular flange 58 and a central cover 59 which includes a central aperture 60 that is sealed by means of a compound O ring sealing assembly. A specimen sample container extractor 62 extends through the aperture 60 and can be vertically reciprocated in the manner described hereinafter. The joint between the flange 58 and the cover 59 is hermetically sealed by means of an O ring 61. A sample egress motor 64 is mounted on the flange 58 and is connected to a sample extractor motor 66 via a link 68. The egress motor 64 is operative to move up and down on a support post 70 which is mounted on the flange 58. The motors 64 and 66 are selectively activated via respective drive lines 74 and 72 which are selectively operated by the system controller computer.

Figure 2:
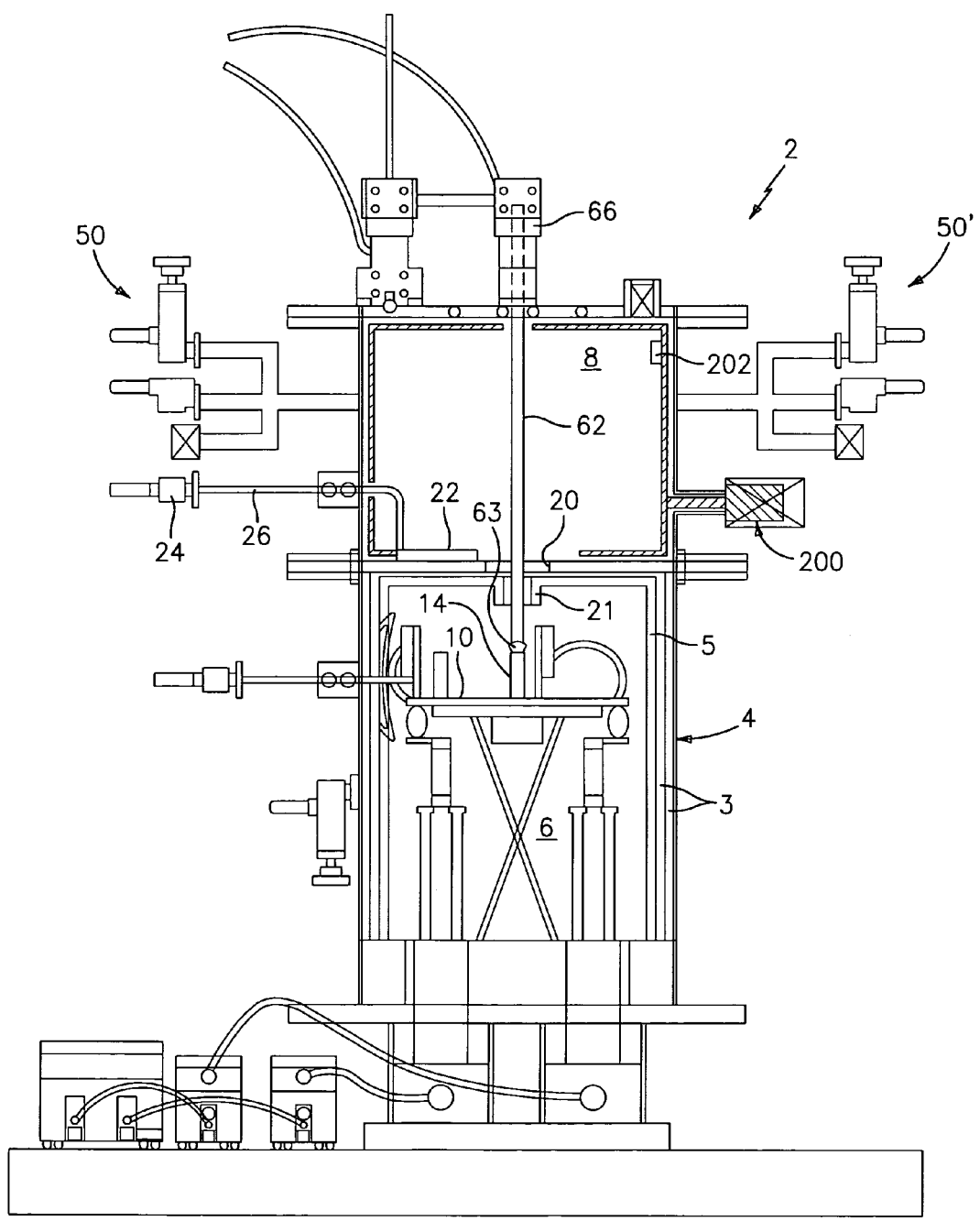
FIG. 2 is a view similar to FIG. 1, but showing a specimen sample container-retrieval condition of the assembly.
Figure 3:
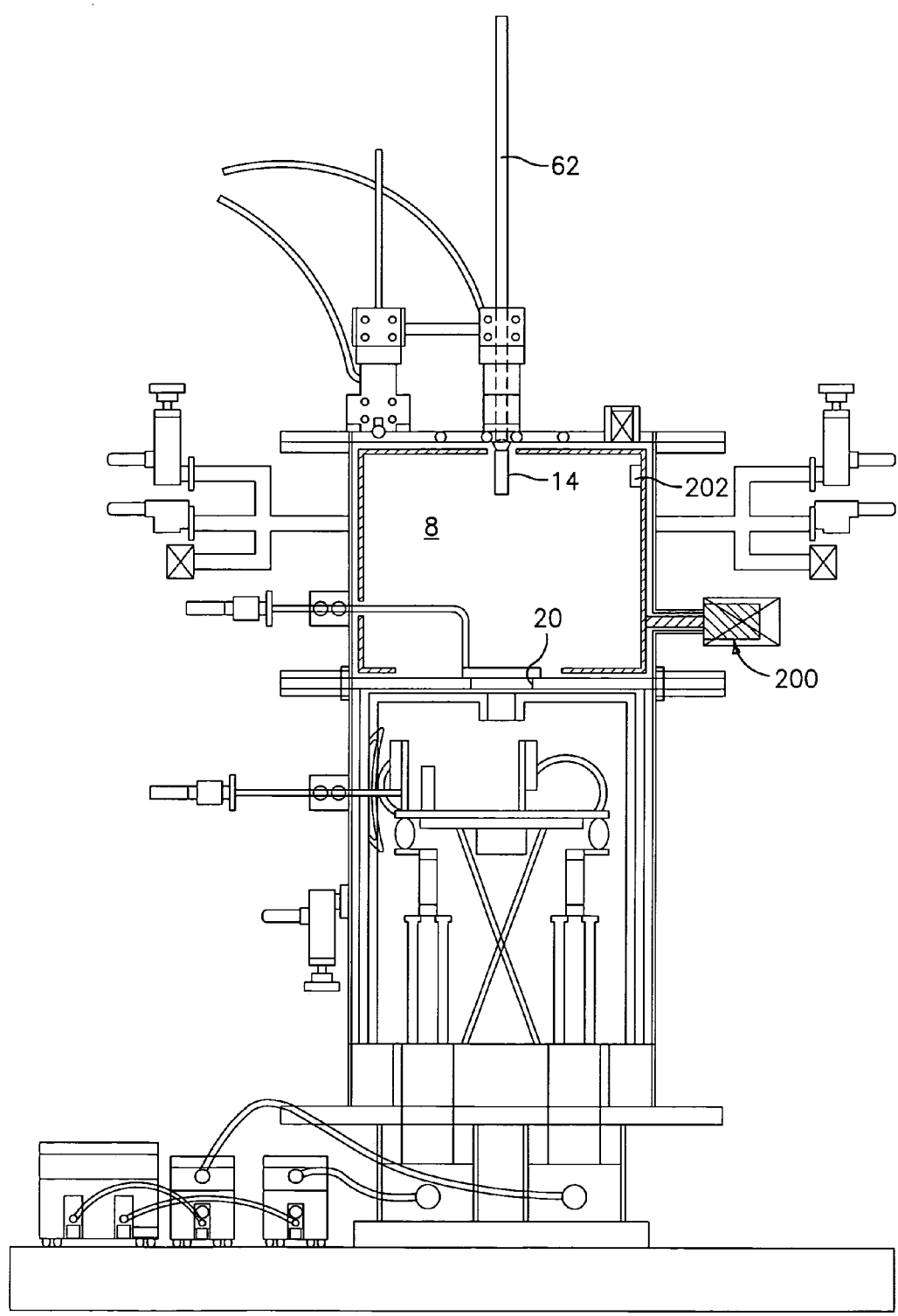
FIG. 3 is a view similar to FIG. 2, but showing a specimen sample container-extraction condition of the assembly.

Referring now to FIGS. 2 and 3, these figures illustrate the manner in which a specimen sample container 14 is removed from the stage 10 in the chamber 6 and placed in the chamber 8, prior to being removed from the assembly 2. When it is desired to remove one of the containers 14 from the chamber 6, the chamber 8 in the assembly 2 is evacuated via the evacuating valves 52 or 52' so as to make the pressure in the chamber 8 equal to the extant pressure in the chamber 6. This evacuation step is performed with the plate 22 in the position shown in FIG. 1. Once the pressure in the chamber 8 equals the pressure in the chamber 6, the pre cooler 200 is turned on. When the sample extractor tip has been cooled to a temperature of about −183° C., the plate 22 is moved by the actuator 24 and rod 26 so as to open the access window 20, as shown in FIG. 2. Then, the motor 66 is activated to lower the extractor 62 through the open window 20 until the extractor tip 63 engages the specimen sample container, as shown in FIG. 2. At this point in time, the pressure in the chambers 6 and 8 are the same. An annular baffle 21 reduces the amount of heat which is absorbed onto the sample containers 14 which heat may be emitted from ambient temperature components within the chamber 8. After the specimen sample tube 14 is engaged by the extractor tip 63, the extractor 62 is lifted along with the tube 14 back through the window 20 up into the chamber 8, and the window 20 is then re-closed, as shown in FIG. 3. The pre cooler 200 is turned off and the temperature of the specimen sample is brought up to ambient temperature. The evacuation valves 52 and 52' are closed and the pressurization valves 54 and 54' are opened. The pressure in the chamber 8 is then brought back up to slightly above ambient pressure. The temperature of the sample 14 is brought up to room temperature in a controlled fashion through the use of a heater connected to the extractor 62. Then the motor 64 is moved up the pole 70 so as to lift the motor 66, by reason of the link 68 between the two motors 64 and 66, and the extractor 62 whereby the retrieved specimen sample 14 is lifted out of the assembly 2 so that it may be removed from the extractor 62. Once the specimen sample 14 is automatically removed from the extractor 62, the motor 64 is returned to its original position on the pole 70 and the extractor 62 is moved back through the opening 60 thereby re-closing the chamber 8. It will be noted that during the entire specimen sample retrieval procedure, the vacuum in the chamber 6 is maintained as is the cryo-preservation temperature, which as noted above can be as low as 4K.

Figure 4:
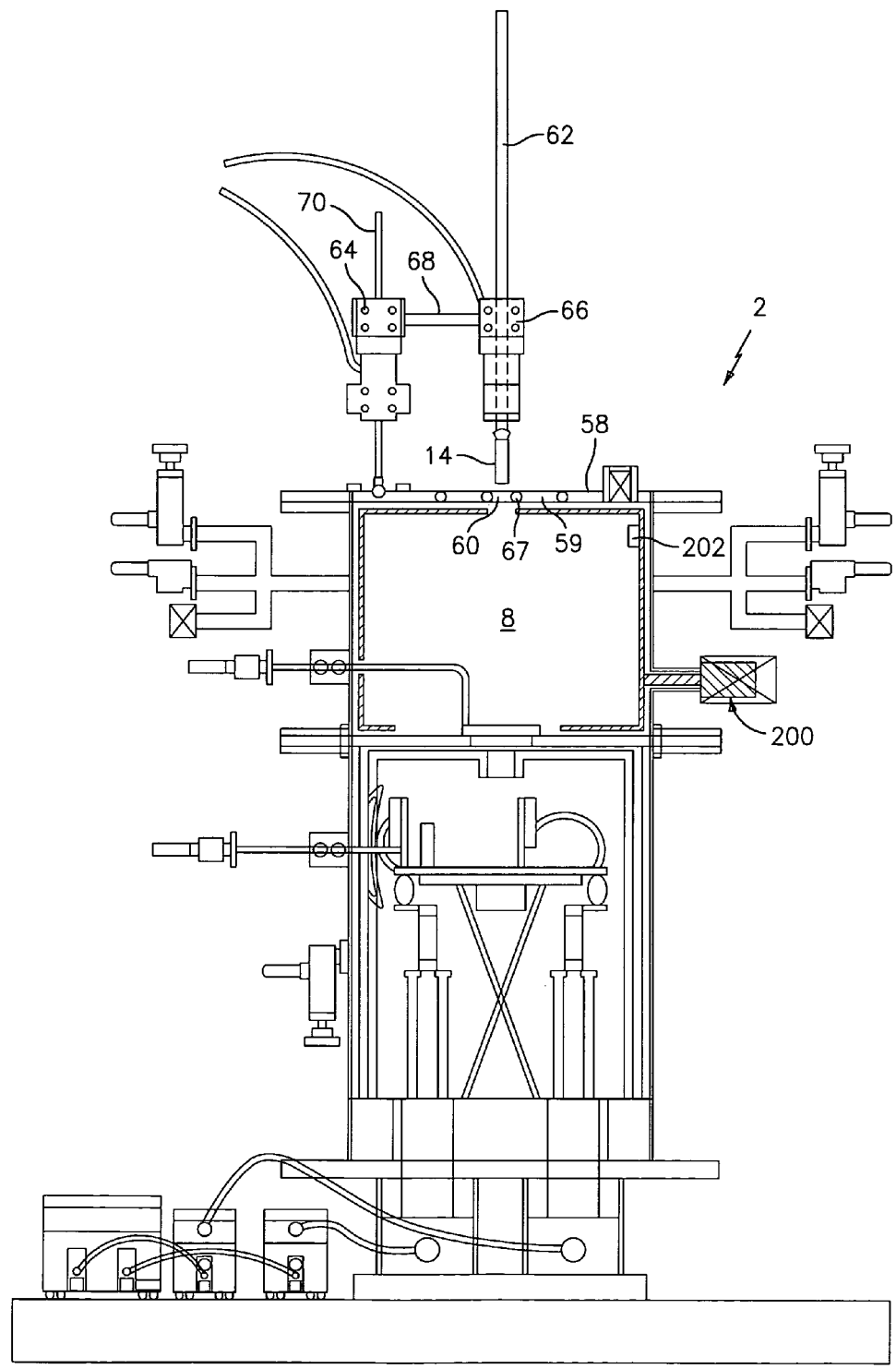
FIG. 4 is a view similar to FIG. 3 but showing the specimen sample container removal condition of the assembly.

Specimen samples 14 are inserted into the assembly 2 in the following manner. An appropriate sample is selected from a number of patient or other identifying samples and it is entered into the system computer controller. Before placing the selected sample on the cryo-stage 10, the evacuation valve 52 is closed and the chamber 8 is slowly filled with dry nitrogen gas through access port 54 at a pressure of slightly greater than ambient thereby creating a chamber pressure which is slightly greater than ambient. The motors 64 and 66 are then actuated to move the extractor 62 and the extractor tip 63 upwardly out of the chamber 8 as shown in FIG. 4. A selected specimen sample tube 14 is then moved from a designated location on an ambient temperature storage rack (shown in detail in FIG. 6) into alignment with the extractor Up 63 so that the specimen sample tube 14 can be picked up by the extractor 62. The motors 64 and 66 are then returned to the position shown in FIG. 1, and the motor 66 is then actuated to lower the selected specimen sample tube 14 down into the chamber 8 to the position shown in FIG. 3. This seals the chamber 8 from the ambient surroundings. Chamber 8 is evacuated by closing pressurization valve 54 and opening evacuation valve 52. The pre cooler 200 is turned on and the sample tube 14 is cooled at a controlled rate to a temperature of approximately −183° C. The actuator 24 is then energized to move the plate 22 to the position shown in FIG. 2 to open the chamber 6, which, as noted above, is evacuated. The stage 10 is moved to a predetermined location in the chamber 6 by the actuator 12, and that location is stored in the system controller computer. The extractor 62 and specimen sample container 14 are then lowered into the chamber 6 to the position shown in FIG. 2 and the specimen sample container 14 is placed on the stage 10 in the predetermined position and the container 14 is released by the extractor 62. The sample and the container 14 are cooled to operating temperatures which is then maintained by the recirculated cryogen as described above. The assembly 2 is then returned to the condition shown in FIG. 1. This procedure is repeated until all of the designated specimen sample containers 14 are properly positioned on the stage 10.

Figure 5:
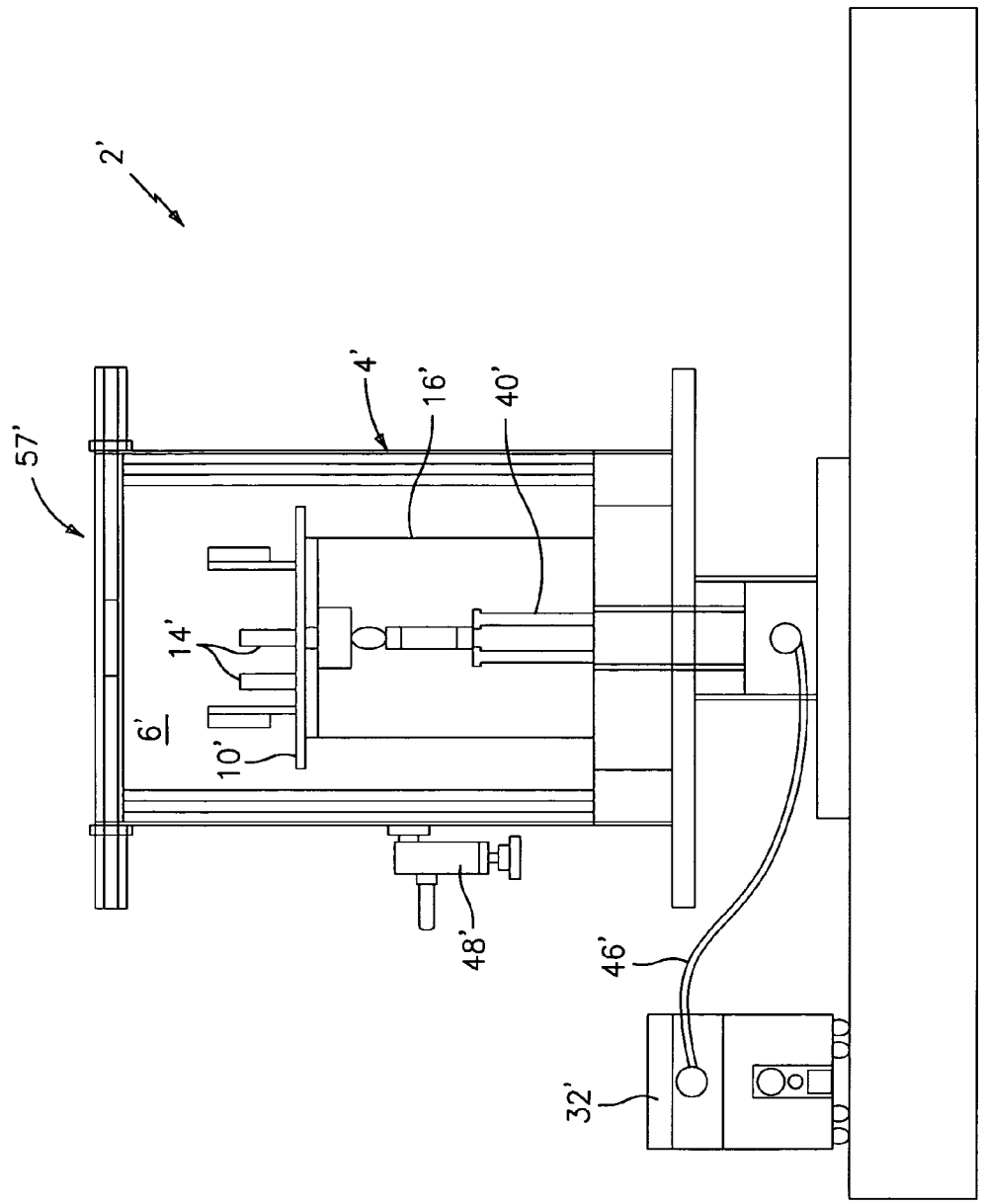
FIG. 5 shows a simplified version of the cryogenic preservation assembly of this invention.

Referring now to FIG. 5, there is shown a second simplified embodiment of a cryogenic preservation assembly which is denoted generally by the numeral 2'. This assembly 2' is not necessarily as fully automated as the previously described assembly 2, but the assembly 2' does share certain similarities with the assembly 2. The assembly 2' includes a housing 4' defining a preservation chamber 6'. The chamber 6' is thermally insulated from the housing 4' and ambient surroundings, as described above in connection with the first assembly 2. The chamber 6' houses a stage support 16' and a specimen sample container stage 10'. The specimen sample containers 14' are positioned on the stage 10'. The assembly 2' also includes a cryogen compressor 32' which is connected to a heat exchanger 40' via line 46'. The heat exchanger 40' is located in the chamber 6'. The chamber 6' can be evacuated and repressurized through means of a vacuum pump (not shown) which is connected to valve 48'. The chamber 6' is thermally insulated in the manner described in connection with the first embodiment of the invention as set forth herein above. The housing 4' includes a removable lid 57' which closes off the chamber 6'.

The assembly 2' operates as follows. With the chamber 6' at ambient pressure and ambient temperature, the lid 57' is removed from the housing 4', and the specimen sample containers 14' are manually placed on the stage 10'. Since this embodiment of the invention is not as completely automated as the previous embodiment, the specimen sample containers 14' can be color coded, or otherwise rendered distinguishable, in a conventional manner so as to distinguish one specimen sample from another. The lid 57' is then replaced, and the chamber 6' is evacuated. The compressor 32' is used to compress the cryogen being used, be it nitrogen, helium, or some other cryogen, to its pressurized state, and the pressurized cryogen is circulated through the heat exchanger 40', expanded in the heat exchanger and then circulated back through the heat exchanger to the compressor 32'. When specimen sample containers 14' are to be removed from the assembly 2', the compressor 32' is momentarily shut down; the sample containers 14' are allowed to warm up to ambient temperature; and the pressure in the chamber 6' is raised to ambient pressure. The lid 57' is then removed and the specimen sample container or containers to be removed are manually removed from the chamber 6'.

Figure 6:
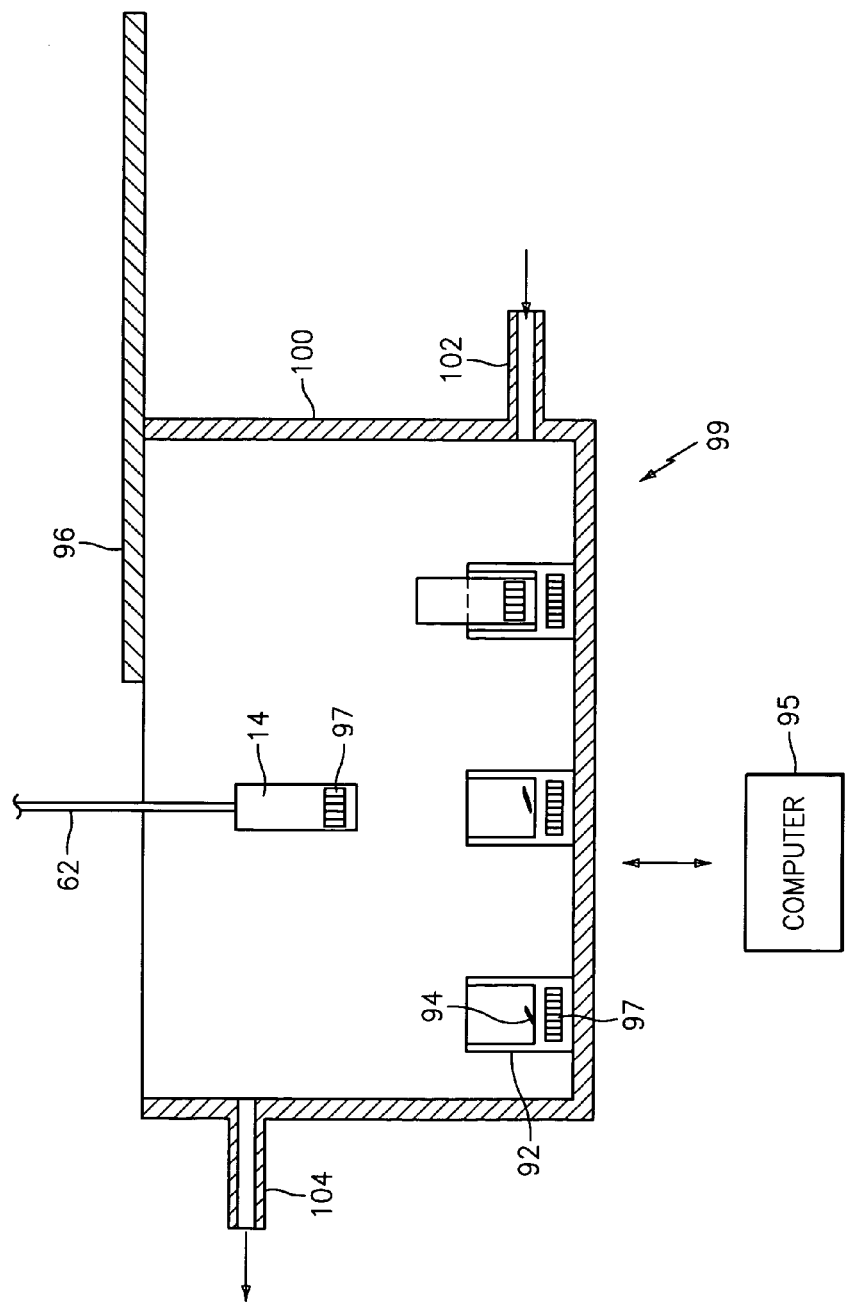
FIG. 6 is a cross sectional view showing details of a specimen sample storage rack.
Figure 7A:
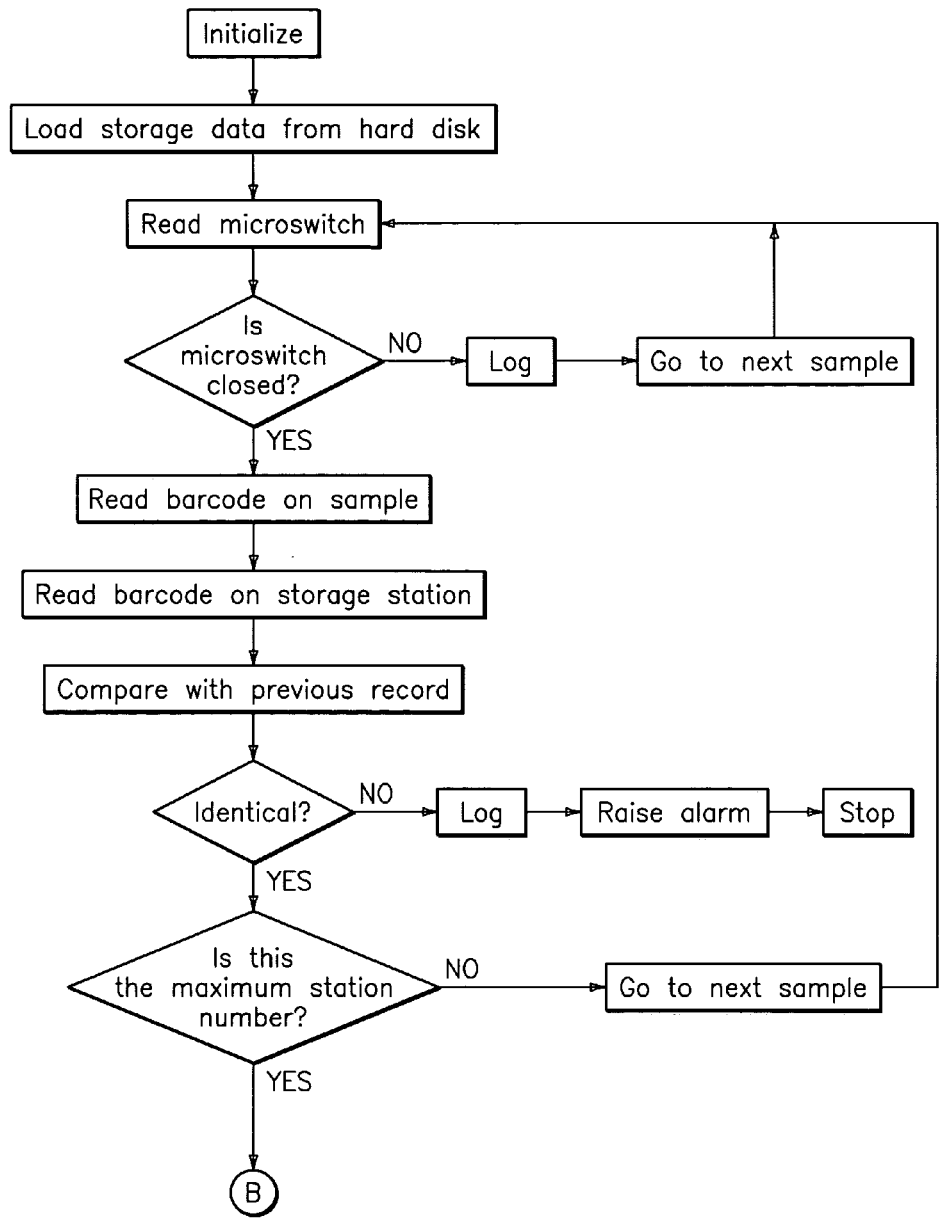
FIGS. 7(a)–(k) are schematic drawings showing the various operating steps during operation of the assembly of this invention.
Figure 7B:
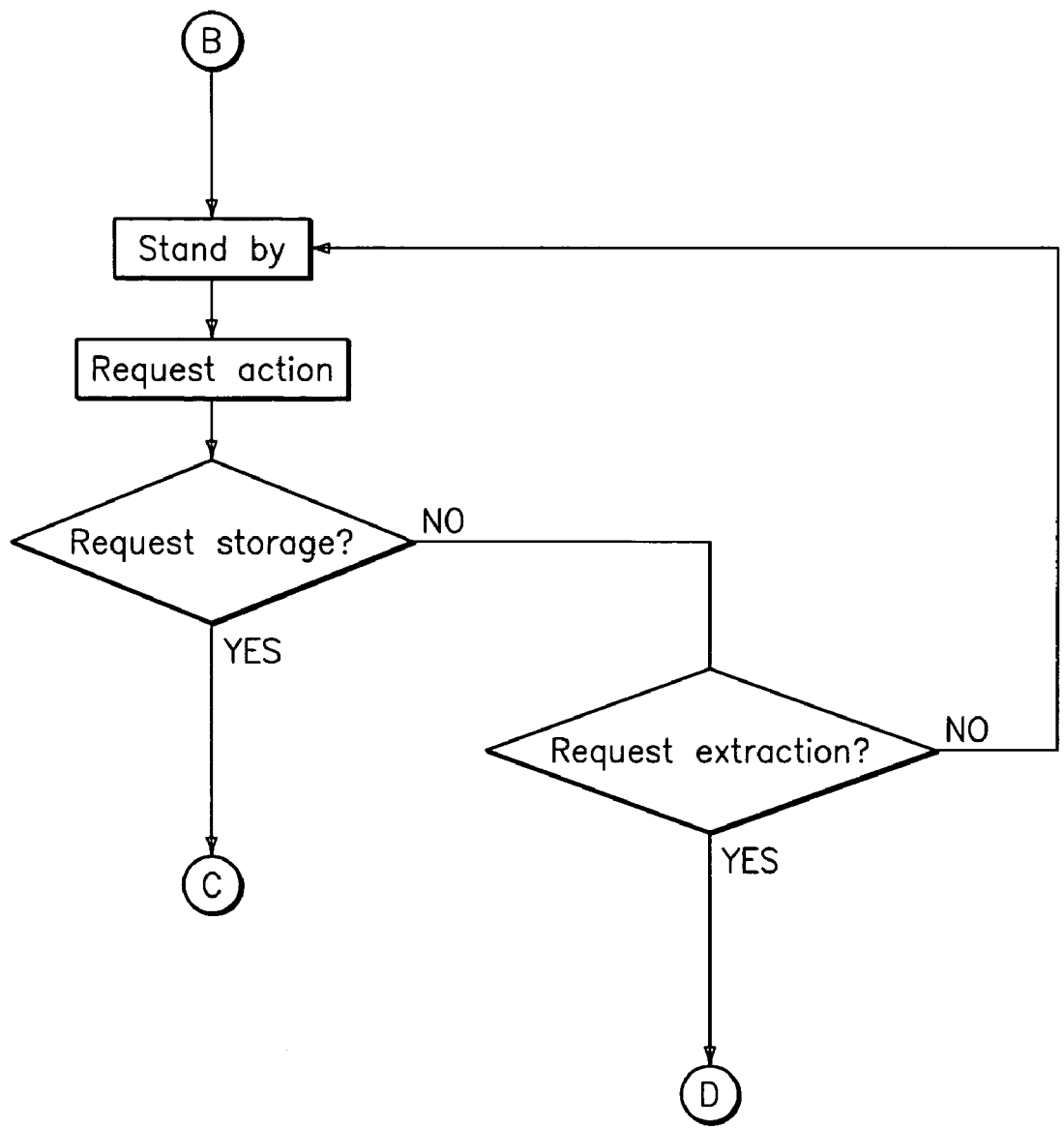
Figure 7C:
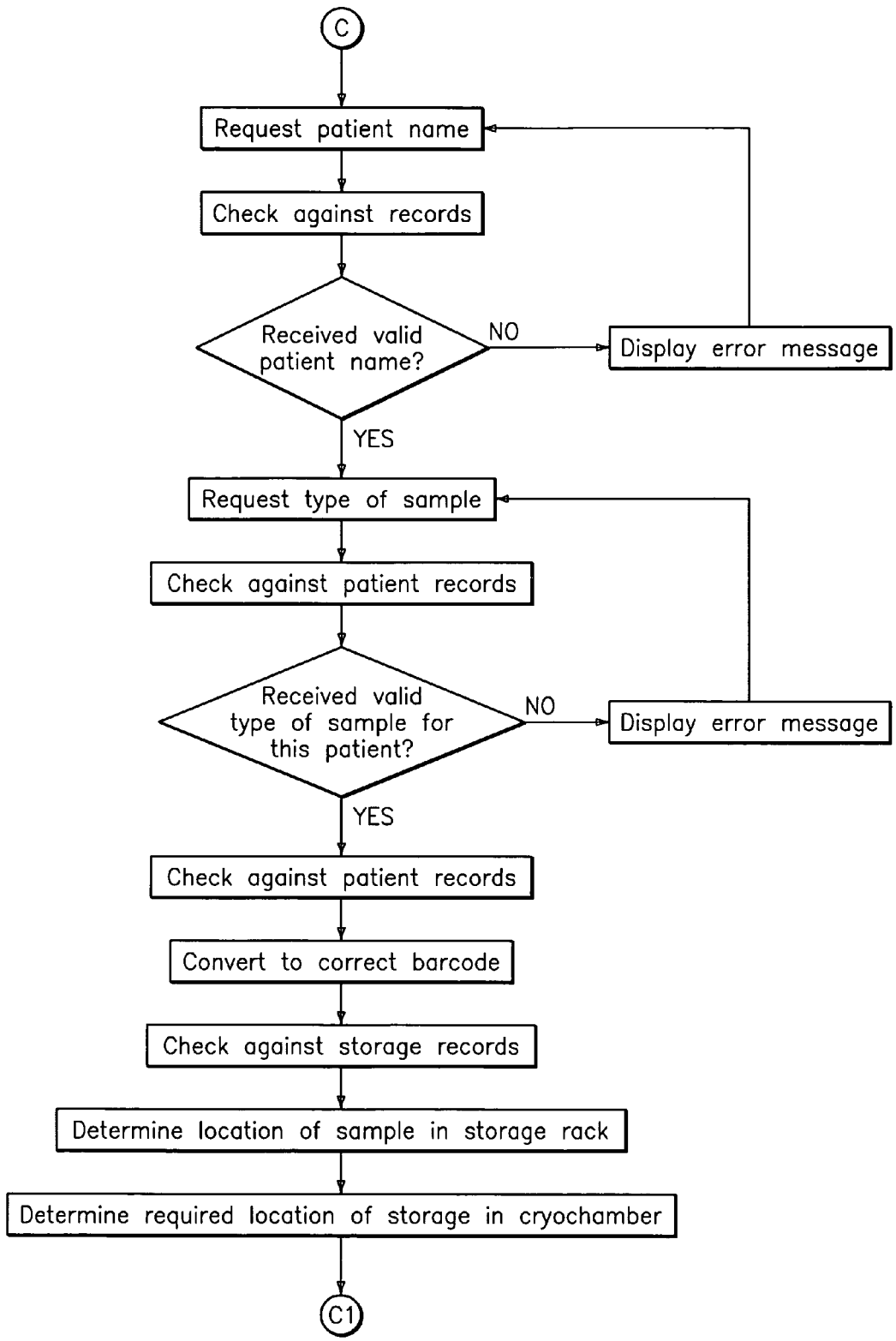
Figure 7D:
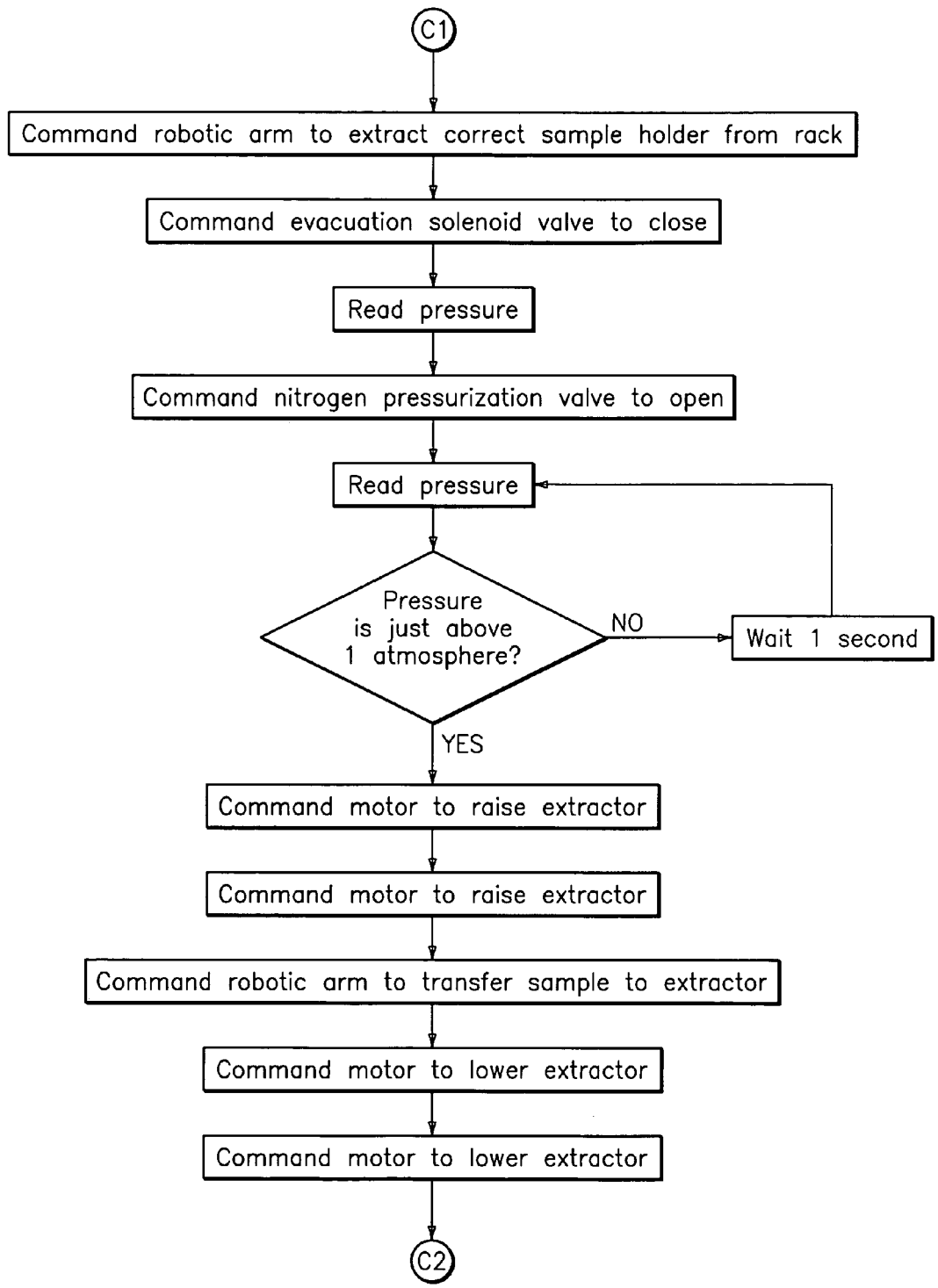
Figure 7E:
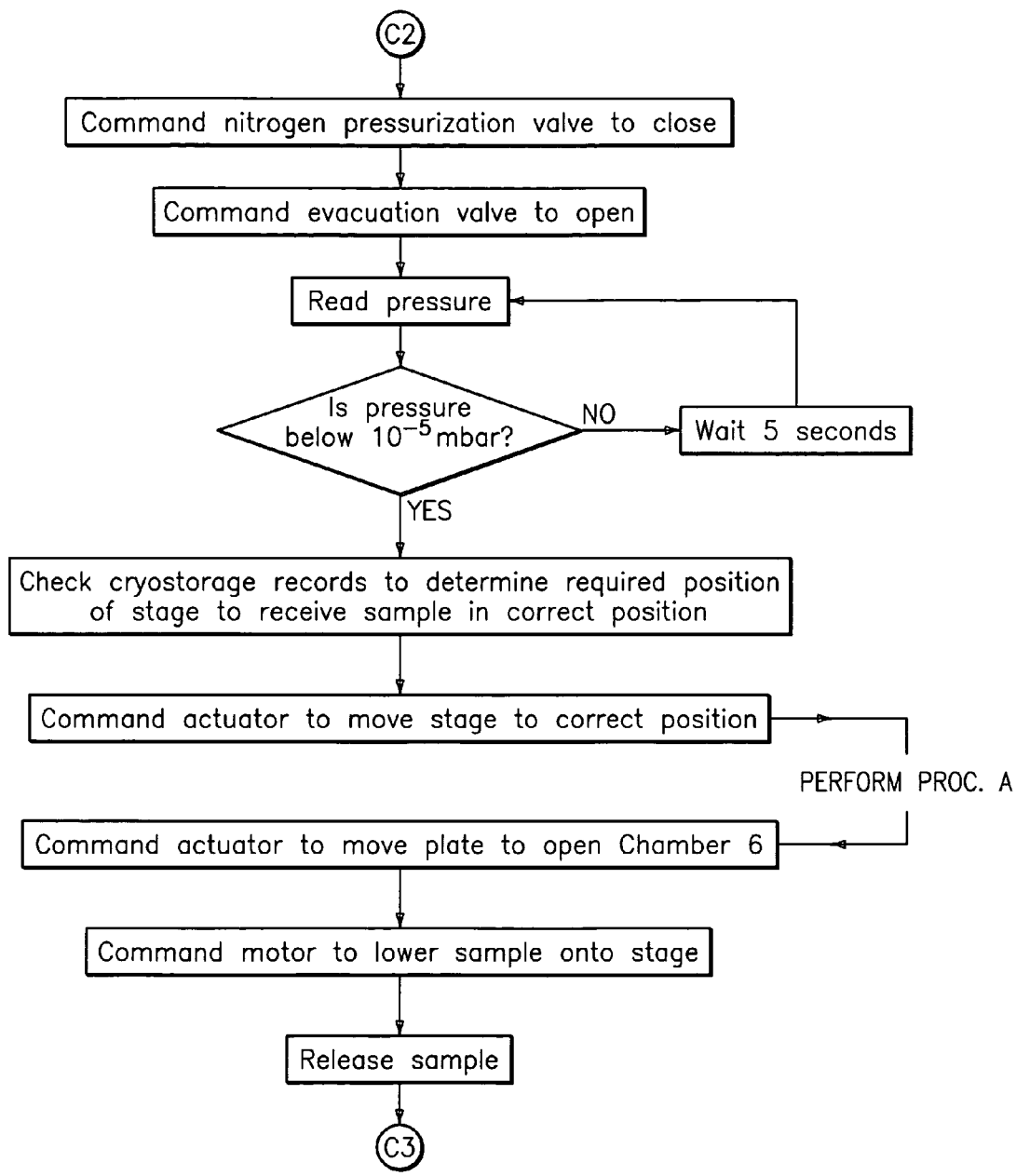
Figure 7F:
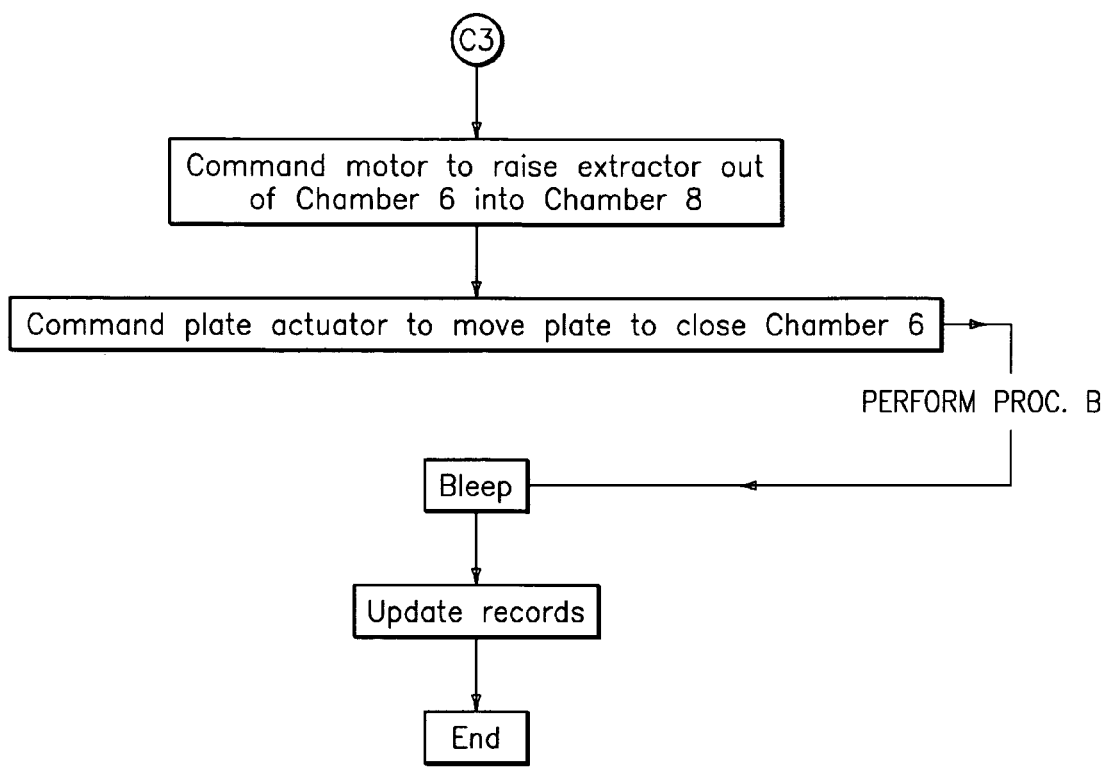
Figure 7G:
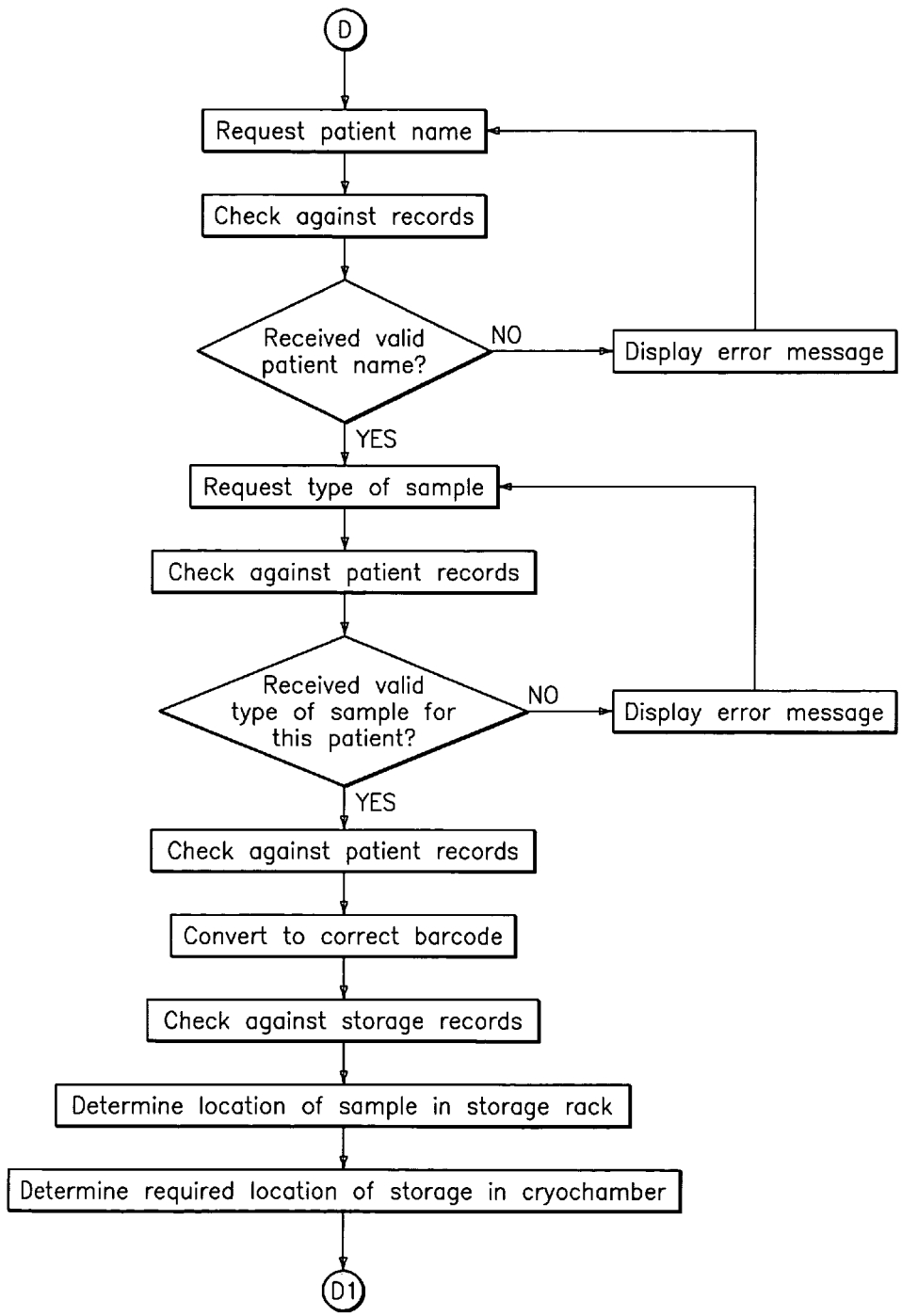
Figure 7H:
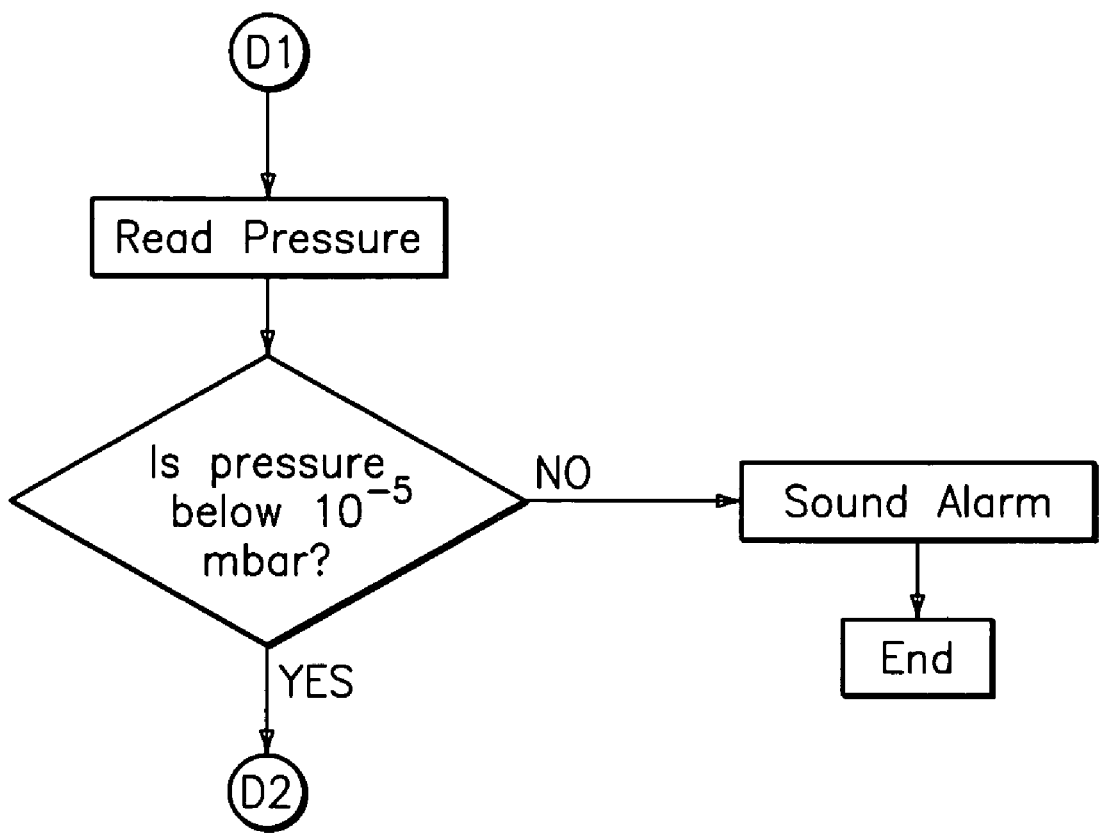
Figure 7I:
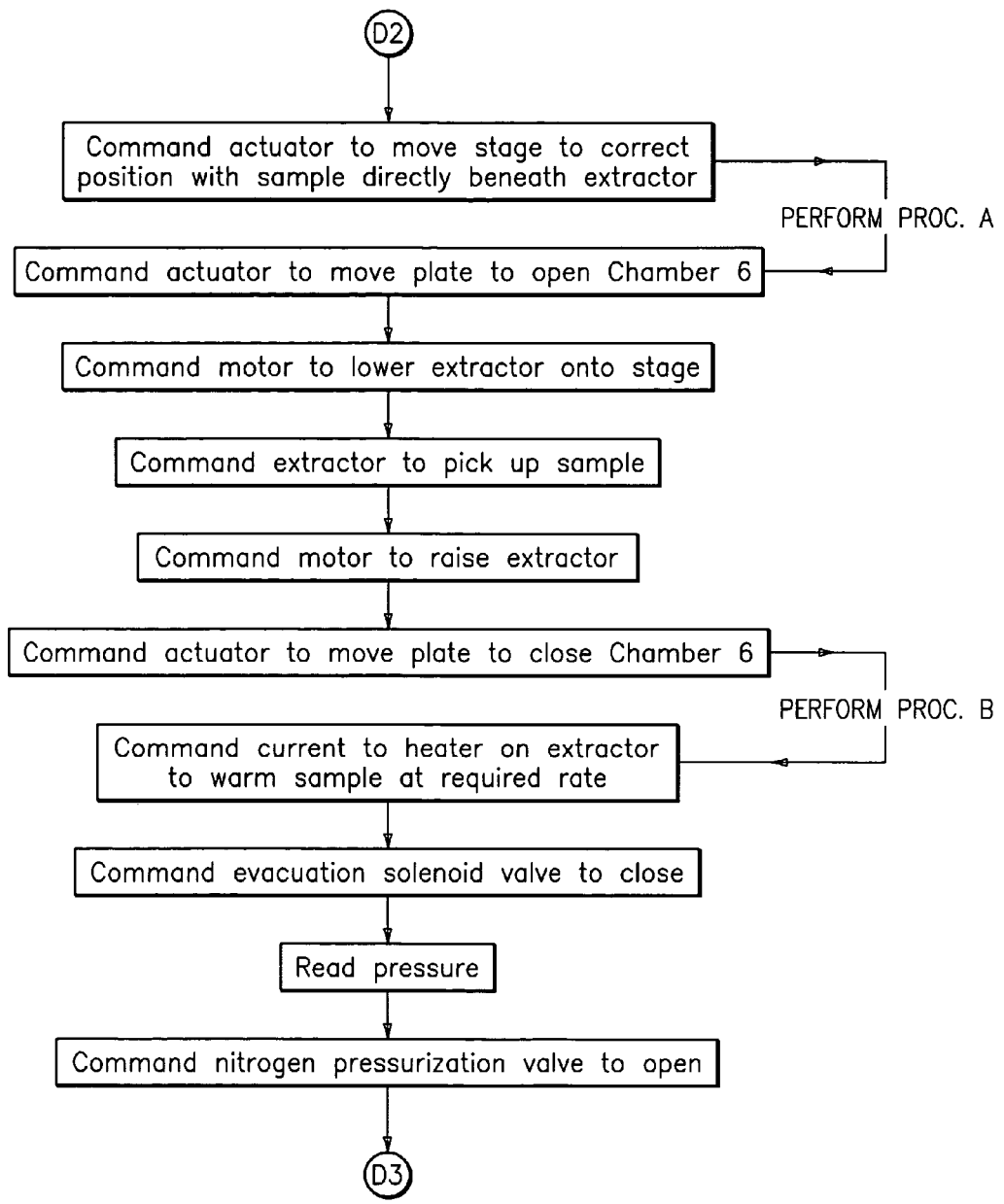
Figure 7J:
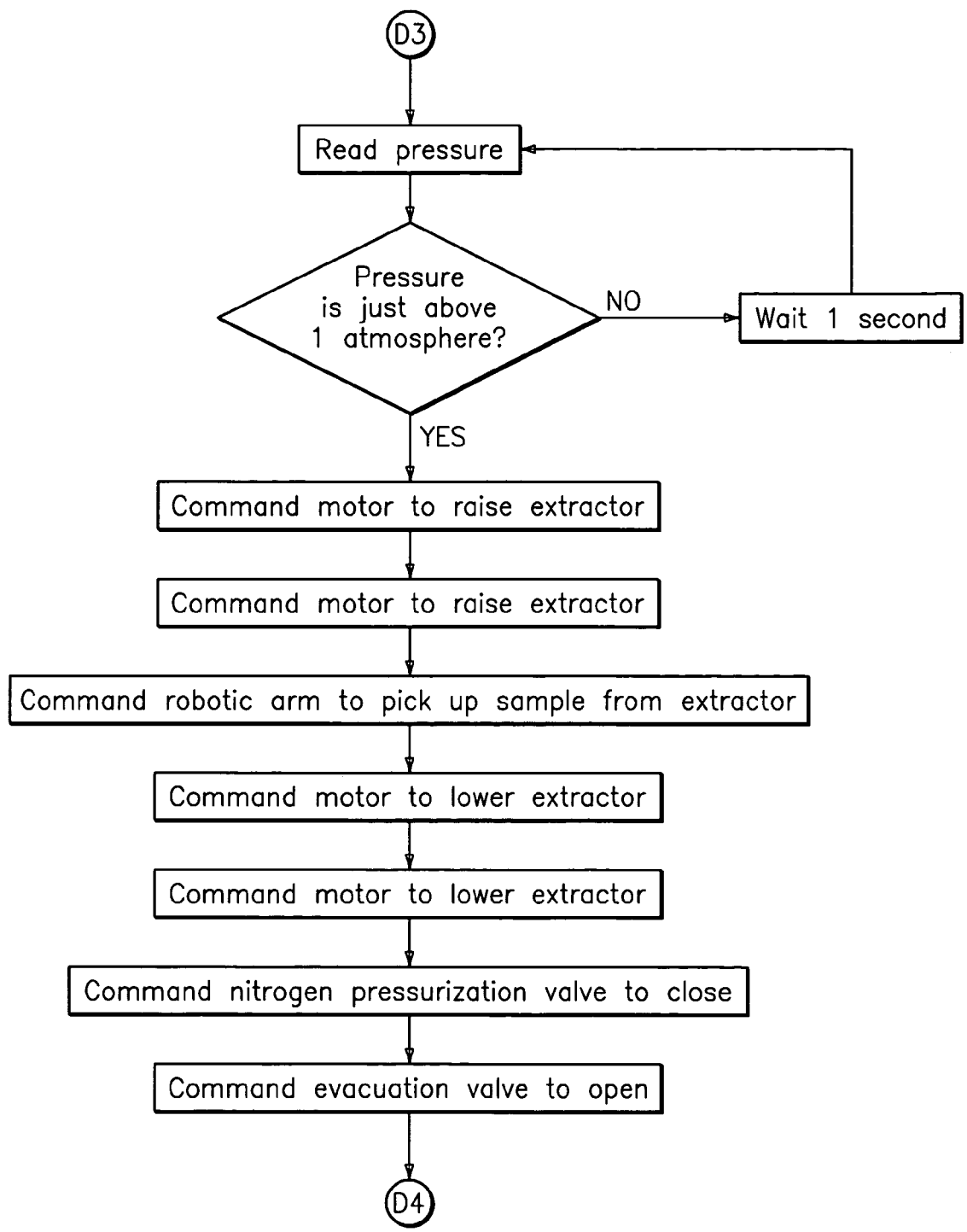
Figure 7K:
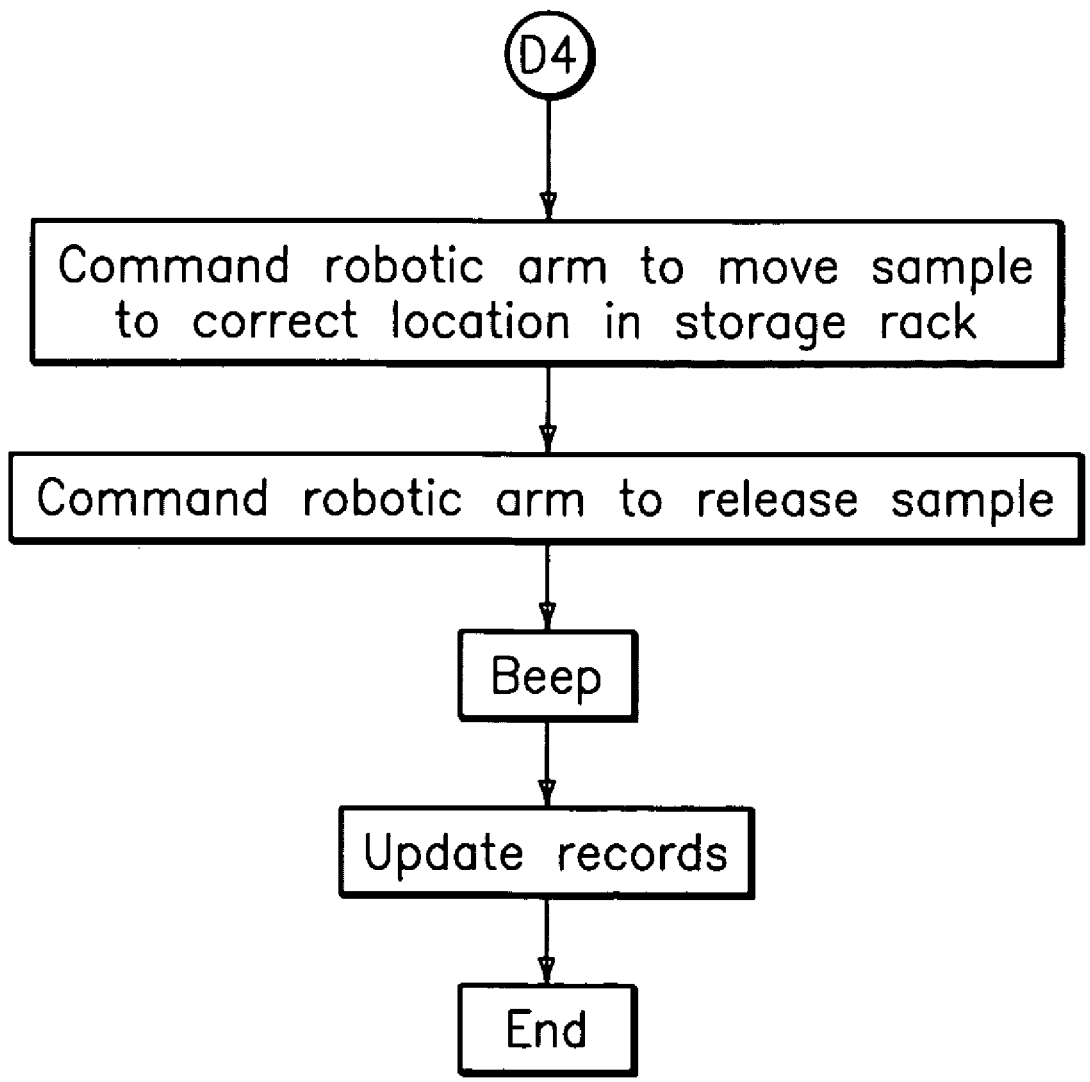

Referring now to FIG. 6, there is shown a preferred embodiment of a specimen sample storage rack, denoted generally by the numeral 99, which can serve as a precursor site for specimen samples which will be placed in the cryogenic freezer 2. The sample storage rack 99 includes a container 100 in which the specimen samples 14 are placed prior to being transferred to the freezer 2. The storage rack 99 also includes a retractable cover 96 which can be selectively opened when specimen samples 14 are to be removed from the rack 99. The container 100 includes a plurality of sample container storage stations 92, each of which has an internal deflectable micro switch 94 which signals a processor controller 95 as to whether a sample container 14 is, or is not, disposed in the storage stations 92. Each of the sample containers 14 is provided with a bar code, or some other machine readable indicia 97 which identifies details of the specimen that is disposed in the container 14. Each of the storage stations 94 also includes a barcode or the like 97 which tracks or traces the barcode 97 on the sample container 14 that is to be deposited in that storage station 94. The container 100 is provided with a dry nitrogen gas purge inlet 102 and a dry nitrogen gas purge outlet 104.

The storage rack 99 operates as follows. Before specimen sample containers 14 are loaded into the container 100. They are picked up by the robotic arm 62 and moved to a location above the container 100 and they are scanned by a bar code scanner (not shown) which is operatively connected to the computer controller 95. The cover 96 is retracted, as shown in FIG. 6, and the robotic arm 62 lowers the sample container 14 into the storage station 92 that has a barcode that correctly tracks or traces the barcode on the container 14 in question. When the micro switch 94 in question doses, the computer controller 95 records the entry of the sample in the storage rack 99. When this procedure is finished, the robotic arm 62 is retracted from the interior of the container 100 and the cover 96 is closed. This procedure is repeated until the requisite number of sample containers 14 are loaded into the storage rack 99. The rack 99 is continuously purged with dry nitrogen gas. When samples 14 are to be retrieved from the rack 99 and placed in the cryogenic preservation assembly 2, the procedure is repeated with the robotic arm 62 transferring selected samples from the rack 99 to the sample support 10 in the cryogenic chamber 6.

The assembly of this invention can be linked with an E-mail port, FAX machine, mobile phone, or the like, so that each time a sample is handled electronically, a message can be sent to the owner(s) of that sample. A digital camera could also be utilized to image the process with recording of the time and date of manipulation of specimen samples. The images could be transmitted to the owner(s) of the samples. This type of sample monitoring would provide the sample owners with updated information relating to the samples in question. Using this procedure, any unauthorized or mistaken handling of specimen samples could be immediately identified and curtailed.

In the case of an automated assembly which is controlled by a system computer controller, the assembly could operate in the following manner, which is schematically shown in FIGS. 7(*a*)–(*k*).

A specimen insertion step protocol into the cryochamber would include the following steps:

1) The operator of the assembly enters the name of the sample and/or the patient whose sample is to be placed in cryogenic storage. The computer controller automatically assigns a specific ID to this sample, which ID will be referred to for purposes of illustration as Sample #2.
2) The solenoid valve to the evacuation pump is closed.
3) The primary chamber 8 is filled with dry nitrogen at a controlled rate until the primary chamber is under a slight positive pressure with respect to ambient pressure.
4) The sample extractor motor is energized so that the plunger tip is moved vertically upwardly away from the closure plate.
5) The sample egress motor is energized to move the plunger upwardly away from the cover.
6) Sample #2 is moved into alignment and engagement with the plunger tip.
7) The sample egress motor is energized so as to move sample #2 downwardly into the upper chamber thereby closing the vacuum/pressure seal between the plunger and the cover.
8) The solenoid valve to the pressurization line is closed.
9) The solenoid valve for the evacuation pump is opened.
10) The primary chamber 8 is evacuated.
11) The linear translator moves in the X direction so that the correct sample container slot for sample #2 is vertically aligned with the plunger.
12) The actuator is energized to move the closure plate in the X direction so as to open the primary chamber 8 to the secondary chamber 6.
13) The sample extractor motor is energized so as to move the sample #2 down into the secondary chamber 6 and into the correct sample container slot. This movement is performed at a controlled rate so as to ensure a prescribed rate of further cooling of the sample.
14) The sample #2 is released from the plunger tip and is placed on the sample container support.
15) The sample extractor motor is energized so as to move the plunger tip vertically into the primary chamber 8.
16) The actuator is energized so as to move the closure plate in the X direction to dose the primary chamber 8 from the secondary chamber 6.

During the aforesaid sequence of operations, the cryogen fluid continues to be compressed in the compressor, to flow through the heat exchanger, to expand in the expansion space in the heat exchanger, and then to expand further as it warms through its return flow through the heat exchanger back to the compressor. The cryogen is repeatedly circulated into the heat exchangers and expanded to cool the specimen samples to the desired cryogen liquefaction temperature and target cryo-preservation temperature.

An automated specimen retrieval step protocol would include the following steps.

1) The name of the person whose specimen sample is to be removed from the assembly is entered into the system controller and the controller determines the correct sample that the inputted information relates to, which will be referred to hereinafter as "sample #1" for identification purposes.
2) The linear translator moves in the X direction so as to position the correct slot in the sample support for sample #1 beneath the plunger.
3) The actuator is energized so as to move the closure plate in the X direction to open the primary chamber to the secondary chamber.
4) The sample extraction motor is energized so as to move plunger tip downwardly into the aligned slot on the sample support member. This movement takes place at a controlled rate to ensure that the plunger tip cools adequately so that uncontrolled warming of sample #1 does not occur upon initial contact between sample #1 and the plunger tip.
5) The plunger tip captures sample #1.
6) The plunger extractor motor is energized so as to move the plunger and sample #1 upwardly into the primary chamber at a controlled rate.
7) The actuator is energized so as to move the closure plate in the X direction whereby the primary chamber is closed off from the secondary chamber. The pre cooler is turned off and a heater in the plunger tip is energized so as to commence warming of the sample #1 at a controlled rate until the sample #1 reaches ambient temperature.
8) The solenoid valve to the evacuation pump is closed.
9) The solenoid valve to the pressurization line is opened.
10) The primary chamber is pressurized at a controlled rate with dry nitrogen to a pressure which slightly exceeds ambient pressure.
11) The sample egress motor is energized so as to move sample #1 upwardly away from the primary chamber cover.
12) Sample #1 is removed from the plunger tip and placed in a designated location in an ambient temperature storage rack.
13) The egress and extractor motors are sequentially energized so as to return the plunger to its initial position in the primary chamber.

Figure 8A:
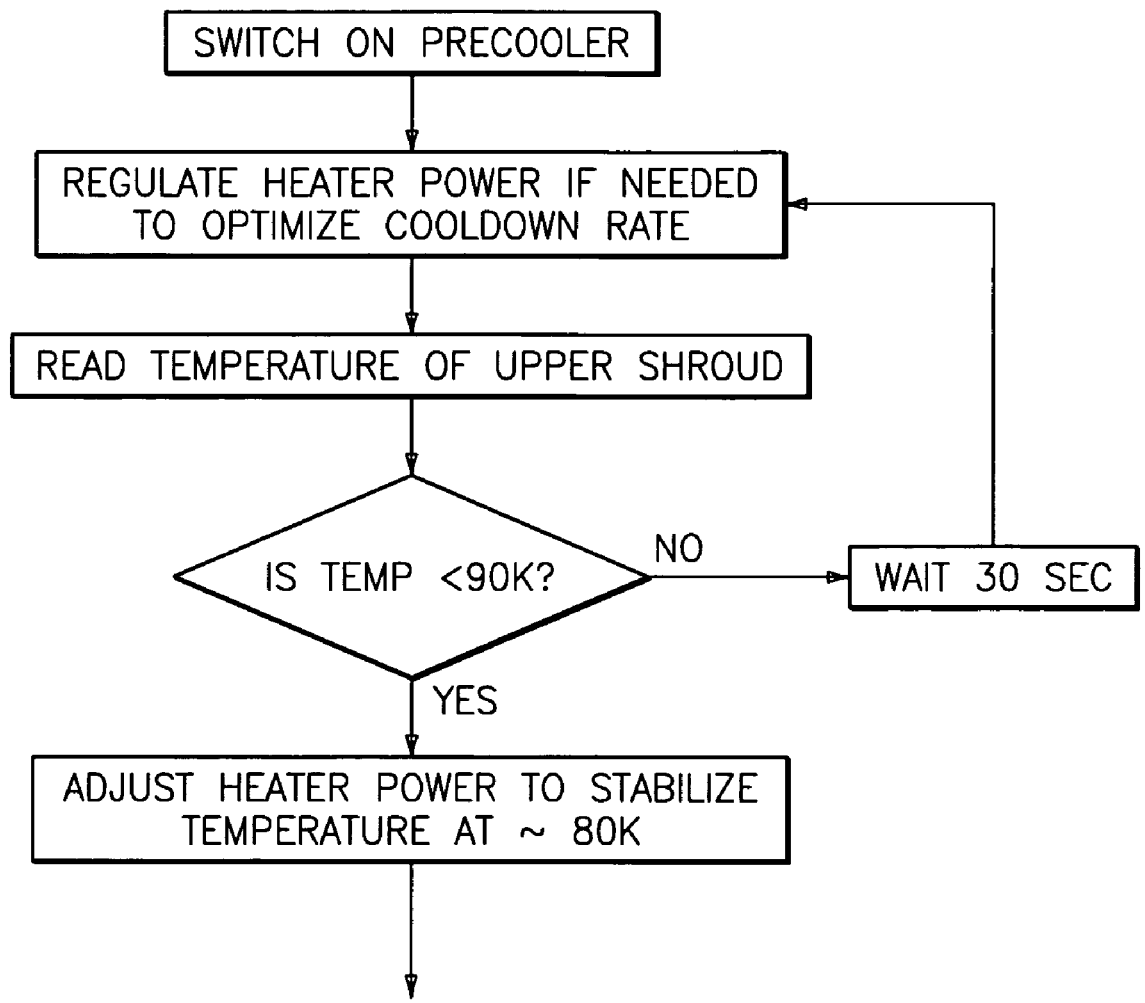
FIG. 8(a) is a schematic drawing of a procedure for providing a preliminary cooling of the upper chamber of the assembly prior to placing specimen samples in the lower chamber of the assembly.

Referring now to FIG. 8(a), the operational steps which make up a preliminary cooling procedure of the upper chamber 8 are shown. This preliminary cooling procedure is referred to herein as Procedure A, and in FIGS. 7(e) and 7(i) as "Proc. A". In the pre cooling procedure, the pre cooler 200 is turned on and the heater 202 is adjusted to a mode which will optimize the cool down rate of the upper chamber 8. The temperature of the upper chamber 8 is periodically checked until it reaches a target cool down temperature, which is preferably less than about −183° C. Once the target cool down temperature is reached, the heater 202 is readjusted so as to maintain the target pre cooling temperature in the upper chamber 8. Specimen samples can then be transferred from the upper chamber 8 into the lower chamber 6 of the assembly 2.

Figure 8B:
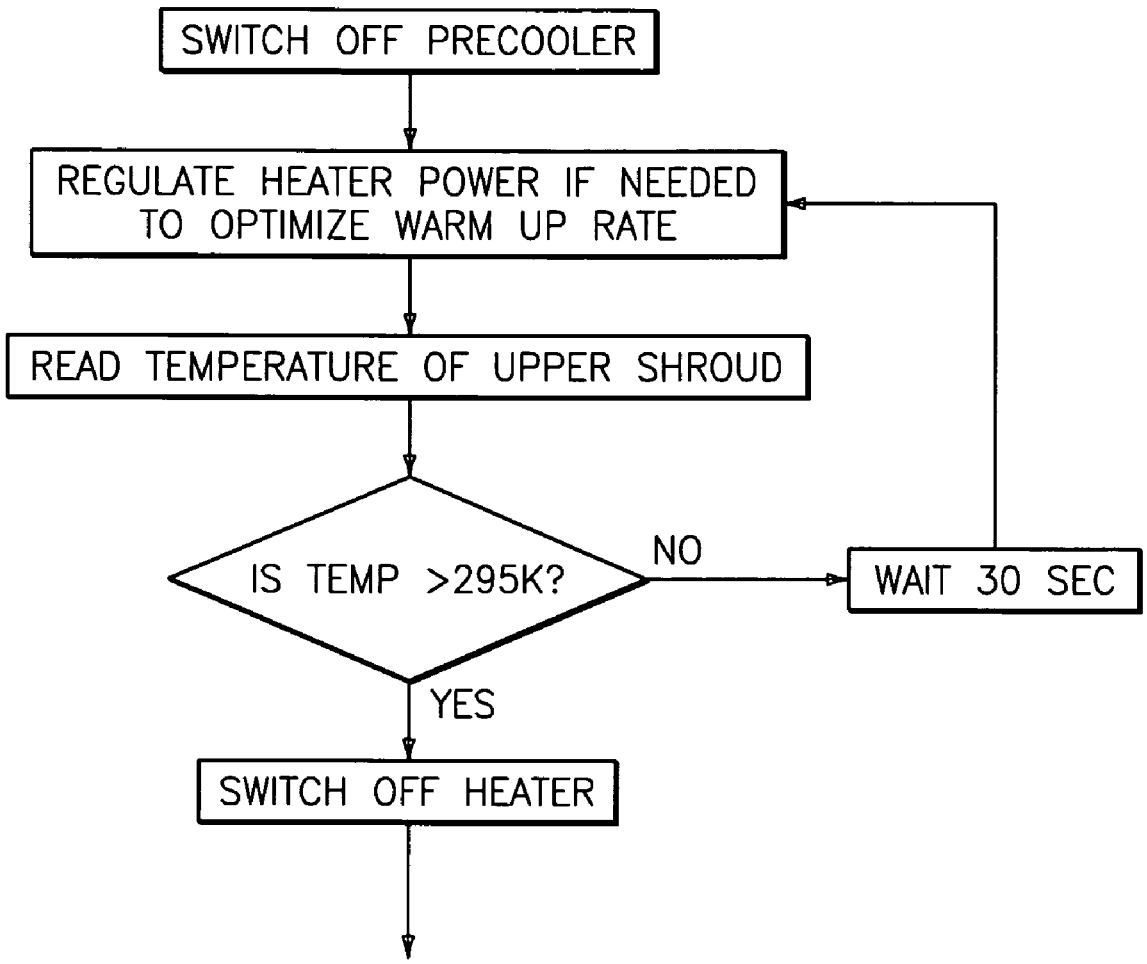
FIG. 8(b) is a schematic drawing similar to FIG. 8(a) but showing a procedure for providing a preliminary warming of the upper chamber of the assembly prior to removing specimen samples from the upper chamber of the assembly.

FIG. 8(b) shows operational steps which make up a preliminary warming procedure of the upper chamber 8. This preliminary warming procedure is referred to herein as Procedure B, and in FIGS. 7(f) and 7(i) as "Proc. B". In the preliminary warming procedure, the pre cooler 200 is turned off and the heater 202 is switched to a mode which will optimize the the warm up rate of the sample 14 when in the upper chamber 8. The temperature of the sample 14 and the temperature in the upper chamber are periodically checked until they both reach ambient temperature. Once ambient temperature is reached, the heater 202 is turned off. Specimen samples can then be transferred from the upper chamber 8 and removed from the assembly 2. The samples will be transferred from the lower chamber 6 to the upper chamber 8 prior to warming of the upper chamber 8 so as not to interrupt the cooling of the other samples which remain in the lower chamber 6.

The assembly and method of this invention provide for cryogenic specimen sample preservation with a minimum chance of sample contamination and a maximum likelihood of maintaining sample integrity and viability. The use of a closed cycle cryogen circulation system ensures that the specimens are never directly exposed to the cryogen and thus cannot be contaminated by the cryogen. The storage chamber in the assembly is evacuated to reduce air-induced heat transfer from the samples to the walls of the storage chamber. The walls of the sample storage chamber are insulated so as to minimize ambient temperature warming of the storage chamber. The assembly of this invention is controlled by an assembly computer controller which ensures that specimen samples are properly identified as to source. The assembly and method of this invention may have the capability of providing the sample source with up to date information regarding storage and handling of the source's specimen sample. Samples can be robotically loaded in the cryogen assembly and robotically removed from the cryogen assembly in a variable fashion, where the rate of cooling and/or warming can be adjusted and programmed to each individual sample or type of sample. While the preferred embodiments of the assembly and method are directed to the cryogenic preservation of cellular samples such as endogenous stem cells, sperm, oocytes and embryos, it will be appreciated that the method of this invention can also be used to preserve non-biological samples including documents, or to provide a closed cycle cryogenically cooled computer environment; and can also be used in the tempering of various materials such as wood or metal.

Since many changes and variations of the disclosed embodiments of the invention may be made without departing from the inventive concept, it is not intended to limit the invention otherwise than as required by the appended claims.

What is claimed is:

1. A method for producing a target temperature for storage of samples in the interior of a sealed container, which target temperature is in the range of about −140° C. to about −269° C., said method comprising the steps of:
   a) placing the samples to be in respective bar-coded receptacles which are positioned on a stage in the sealed container;
   b) compressing a gaseous cryogen;
   c) circulating the compressed cryogen through a closed circuit to at least one sealed heat exchanger which is disposed in the interior of the sealed container so as to lower the temperature of one or more samples disposed in the sealed container;

d) expanding the compressed cryogen in an expansion space in the heat exchanger;
e) recompressing the expanded cryogen;
f) recirculating the recompressed cryogen through the closed circuit to the closed heat exchanger; and
g) repeating steps d) through f) until the target temperature in the sealed container is produced.

2. The method of claim 1 wherein said compressed cryogen liquifies in the expansion space after the expansion space reaches a predetermined cryogen liquefaction temperature.

3. The method of claim 1 further comprising the step of evacuating the interior of the sealed container so as to minimize heat transfer between walls of the container to the heat exchanger.

4. The method of claim 1 wherein the cryogen is helium.

5. The method of claim 1 wherein the cryogen is nitrogen.

6. The method of claim 1 further comprising the step of insulating walls of the container so as to minimize heat transfer from ambient surroundings to the interior of the container.

7. The method of claim 3 further comprising the step of preliminarily cooling the interior of said sealed container after said evacuating step and prior to performing step c).

8. A system for storing specimen samples at a target temperature which target temperature is in the range of about $-140°$ C. to about $-269°$ C., said system comprising:
a) a sealed specimen sample storage container which can be selectively opened so as to allow specimen samples to be placed in and removed from said container;
b) means for selectively evacuating the interior of said container;
c) at least one heat exchanger disposed in said container;
d) at lease one compressor disposed externally of said container, said compressor being operative to compress a gaseous cryogen;
e) means for continuously circulating the cryogen in a closed loop between said compressor(s) and said heat exchanger(s), whereby compressed cryogen is circulated from said compressor(s) to said heat exchanger(s) and expanded gaseous cryogen is circulated from said heat exchanger(s) to said compressor(s) until said target temperature is reached in said heat exchanger(s); and
f) an inner transverse plate that divides the container into upper and lower chambers, the lower chamber of which contains said heat exchanger(s), said transverse plate having an aperture interconnecting said upper and lower chambers.

9. The system of claim 8 further including a cover for selectively opening and closing said aperture.

10. The system of claim 8 further including a cooling element in said upper chamber for use in preliminarily cooling said upper chamber after inserting a specimen sample into said upper chamber, and prior to transferring a specimen sample from said lower chamber to said upper chamber.

11. The system of claim 10 further including a warming element in said upper chamber for use in warming said upper chamber subsequent to transferring a specimen sample from said lower chamber to said upper chamber whereby said transferred specimen sample is warmed to substantially ambient temperature.

12. The system of claim 8 wherein said upper chamber includes a top cover plate for sealing said upper chamber from ambient surroundings, said plate having an access opening which is aligned with said transverse plate aperture, and an automated vertically reciprocally moveable plunger extending through said access opening, said plunger being operative to selectively load specimen sample receptacles into said storage container and selectively remove specimen sample receptacles from said storage container.

13. The system of claim 12 wherein said lower chamber contains a specimen sample receptacle-supporting stage which is thermally connected to said heat exchanger(s) and which is positioned beneath said aperture in said transverse wall.

14. The system of claim 13 wherein said stage is connected to a driver which is operative to selectively move said stage transversely in said storage container whereby a plurality of specimen sample receptacles can be deposited side-by-side on said stage through said aperture.

15. The system of claim 14 further comprising a plunger driver which is operative to selectively move said plunger vertically between a first position wherein a specimen sample receptacle-engaging tip of said plunger is located in said upper chamber, and a second position wherein the tip of said plunger is located in said lower chamber.

16. The system of claim 15 further comprising means for moving said plunger driver up and down so as to selectively position said plunger tip either above said cover plate and out of said container, or below said cover plate and in said upper chamber.

* * * * *